(12) United States Patent
Samsonov et al.

(10) Patent No.: US 10,807,997 B2
(45) Date of Patent: Oct. 20, 2020

(54) METHODS FOR MAKING QUINOLINYLDIAMINES

(71) Applicant: ExxonMobil Chemical Patents Inc., Baytown, TX (US)

(72) Inventors: Oleg V. Samsonov, Moscow (RU); Mikhail I. Sharikov, Moscow (RU); Georgy P. Goryunov, Moscow (RU); Dmitry V. Uborsky, Moscow (RU); Alexander Z. Voskoboynikov, Moscow (RU); Michelle E. Titone, Houston, TX (US); John R. Hagadorn, Houston, TX (US); Jo Ann M. Canich, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/550,847

(22) Filed: Aug. 26, 2019

(65) Prior Publication Data
US 2020/0071344 A1    Mar. 5, 2020

Related U.S. Application Data

(60) Provisional application No. 62/723,817, filed on Aug. 28, 2018.

(51) Int. Cl.
| | | |
|---|---|---|
| *C07D 215/00* | (2006.01) | |
| *C07D 215/40* | (2006.01) | |
| *C07F 7/00* | (2006.01) | |
| *C08F 4/76* | (2006.01) | |
| *C07C 209/60* | (2006.01) | |
| *C07F 5/04* | (2006.01) | |
| *C07C 221/00* | (2006.01) | |
| *C07C 201/08* | (2006.01) | |
| *C07C 45/65* | (2006.01) | |

(52) U.S. Cl.
CPC ............... *C07F 7/00* (2013.01); *C07C 45/65* (2013.01); *C07C 201/08* (2013.01); *C07C 209/60* (2013.01); *C07C 221/00* (2013.01); *C07D 215/40* (2013.01); *C07F 5/04* (2013.01); *C08F 4/76* (2013.01); *C07C 2602/08* (2017.05); *C07C 2602/10* (2017.05)

(58) Field of Classification Search
CPC ............................. C07D 215/00; C07D 215/40
USPC .................................................. 546/152, 10
See application file for complete search history.

(56) References Cited

U.S. PATENT DOCUMENTS

| | | |
|---|---|---|
| 6,103,657 A | 8/2000 | Murray |
| 6,900,321 B2 | 5/2005 | Boussie et al. |
| 7,687,672 B2 | 3/2010 | Buchanan et al. |
| 7,858,833 B2 | 12/2010 | Buchanan et al. |
| 7,982,085 B2 | 7/2011 | Buchanan et al. |
| 8,003,839 B2 | 8/2011 | Buchanan et al. |
| 8,076,524 B2 | 12/2011 | Lattner et al. |
| 8,212,047 B2 | 7/2012 | Hagadorn et al. |
| 10,208,140 B2 | 2/2019 | Hagadorn et al. |
| 2015/0141601 A1 | 5/2015 | Hagadorn et al. ........ C08F 4/76 |

FOREIGN PATENT DOCUMENTS

WO    2018005201    *    1/2018

OTHER PUBLICATIONS

Cottet et al. (2003) "Recommendable Routes to Trifluoromethyl-Substituted Pyridine- and Quinolinecarboxylic Acids," European Journal of Organic Chemistry, v.2003(8), pp. 1559-1568.
Bradley, Wm. et al. (1951) "Chemistry of Indanthrone. V. tert-Butyl Derivatives of Indanthrone and Flavanthrone. The Mode of Formation of Flavanthrone in the Alkali Fusion of 2-Aminoanthraquinone," Jrnl. of Chem. Soc., p. 2176.
Poon, P. S. et al. (2014) "Synthesis of 8-methyl-1-tetralone, a Potential Intermediate for (+/−)-platyphyllide ," Natural Prod. Res., v. 28(20), pp. 1747-1753.
Sheng, M. et al. (2015) "Reactive Chemical Hazards of Diazonium Salts," Jrnl. of Loss Prevention in the Process Ind., v. 38, pp. 114-118.
Suzuki, Kazuo et al. (1963) "Some Observations on the Synthesis of 3-Bromfluorenone," Bull. of Chem. Soc. of Japan, v. 36(12), pp. 1693-1694.
Suzuki, Kazuo et al. (1963) "Studies on Fluorene Derivatives. XXI. The Radical Bromination of Dibiphenyleneethane and its Derivatives by N-Bromosuccinimide," CAS, Database accession No. 1964:38639 v. 36(12), pp. 1654-1657.
*European Search Report* dated Apr. 24, 2019, 11 pgs.
*International Search and Written Opinion* dated Dec. 11, 2019, 10 pgs.

* cited by examiner

*Primary Examiner* — Niloofar Rahmani
(74) *Attorney, Agent, or Firm* — Catherine L. Bell

(57) ABSTRACT

The present disclosure provides methods for making quinolinyldiamine products from quinolinyl starting materials. In addition, the quinolinyldiamines can be used as ligands or ligand precursors for catalysts, e.g. for use in olefin polymerization.

31 Claims, 1 Drawing Sheet

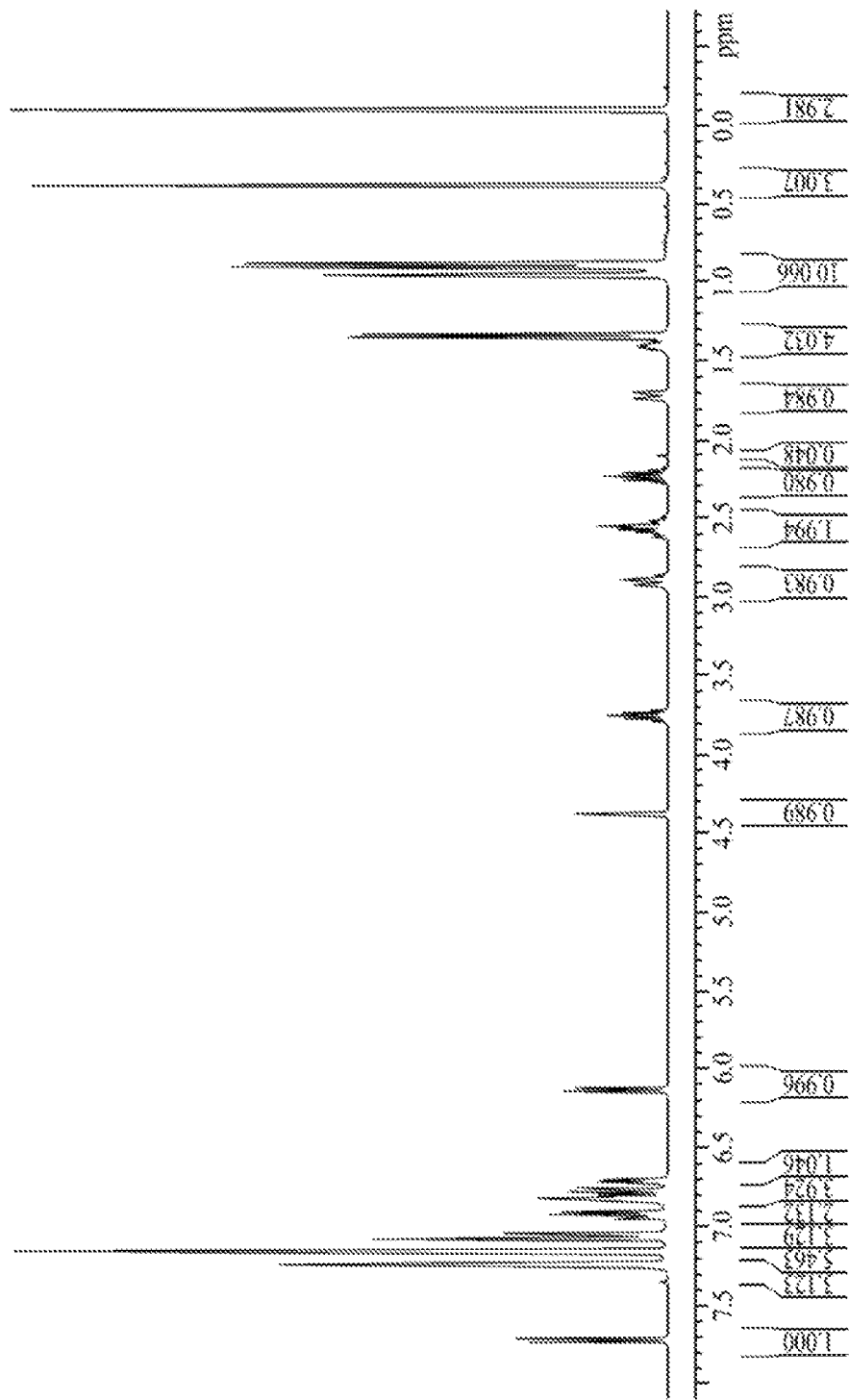

METHODS FOR MAKING QUINOLINYLDIAMINES

CROSS-REFERENCE TO RELATED APPLICATIONS

This application claims priority to and the benefit of U.S. Ser. No. 62/723,817, filed Aug. 28, 2018 and is incorporated by reference in its entirety.

FIELD

The present disclosure provides methods for making quinolinyldiamine compounds, intermediates used in the making thereof and uses.

BACKGROUND

To date, the importance of polymers has been highlighted due to their applications in various technologies and industries—from basic uses to synthetic polymers, biopolymers and therapeutic polymers. Polymers are typically formed using catalysts. The polyolefin industry is one prominent example of the importance of catalysts. A catalyst's ligand(s) greatly influences the effectiveness and the performance of the catalyst in a specific polymerization reaction and the relative importance of ligand bulk and electron-donating ability in the high activity of catalysts derived from the type and characteristics of the ligands. Hence, it has been of a great interest to develop efficient, cost-effective and scaled up processes for ancillary ligands for catalysts for use in olefin polymerization.

Pyridyl amines, especially quinolinyl amines, such as quinolinyldiamines, have been used to prepare Group 4 complexes which are useful transition metal components in the polymerization of alkenes, see, for example, U.S. Pat. Nos. 6,900,321; and 6,103,657. The ligands have been used in complexes in which the ligands are coordinated in a bidentate fashion to the transition metal atom.

Quinolinyldiamines (QDAs) are important, commercially desirable ligands. Quinolinyl amines have been used in a variety of applications, such as in catalytic compositions, and methods of forming such catalytic compositions, which can be found, e.g., in U.S. Pat. Nos. 10,208,140 and 8,212,047. These patents disclose ligands, complexes, compositions and/or catalysts that provide enhanced olefin polymerization capabilities based on a substituted quinolinyldiamine structure and hafnium or zirconium. Other examples of methods of using pyridylamine-containing catalytic compositions for oligomerization reactions can be found, e.g., in U.S. Pat. Nos. 7,858,833, 8,003,839, 7,982.085, 8,076,524, and 7,687,672. However, current methods to synthesize these ligands (and metal-containing analogues) involve large scale syntheses, which usually involve large amounts of silica and/or alumina for purifications by column chromatography of the intermediates and ligands, hence involving a considerable amount of waste and a cost for manufacturing. Syntheses of quinolinyldiamine compounds can often depend on the nature of the substitutions on various portions of the quinolinyl amine molecule. For example, the current synthetic route to QDA ligand precursors involves multiple steps and at least three separate purification steps that require the use of column chromatography over silica or alumina gel.

Though some quinolinyldiamines can be manufactured by synthesis routes that are acceptable for bench-scale syntheses, there is a need for alternate synthesis routes that have economic and scale-up advantages for commercial-scale applicability.

SUMMARY

The present disclosure provides methods for making quinolinyldiamine compounds, intermediates used in the making thereof and uses.

In at least one embodiment, a method for making a quinolinyldiamine, includes:

introducing an acid solution, a nitrite, and a phosphate to a compound represented by Formula C or Formula K

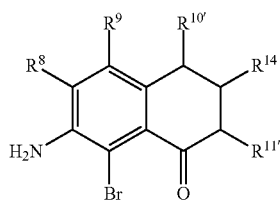

C

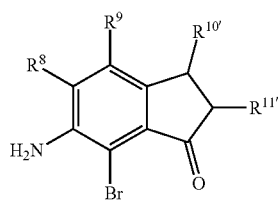

K wherein $R^8$, $R^9$, $R^{10'}$, $R^{11'}$, and $R^{14}$ are independently hydrogen, hydrocarbyl, alkoxy, silyl, amino, aryloxy, substituted hydrocarbyl, halogen, or phosphino, or any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated; and obtaining a compound represented by Formula D or Formula L

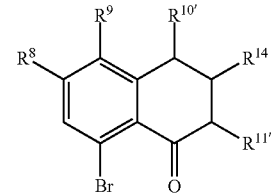

D

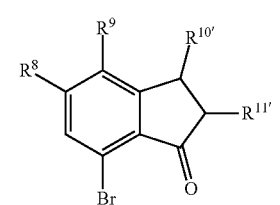

L wherein $R^8$, $R^9$, $R^{10'}$, $R^{11'}$, and $R^{14}$ are independently hydrogen, hydrocarbyl, alkoxy, silyl, amino, aryloxy, substituted hydrocarbyl, halogen, or phosphino, or any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated.

BRIEF DESCRIPTION OF THE DRAWING

The FIGURE is a 400 MHz $^1$H-NMR spectrum of complex QDA-1 solution (ca. 0.01 M in $C_6D_6$) at ambient temperature, according to one embodiment.

DETAILED DESCRIPTION

Methods of the present disclosure can provide syntheses of quinolinyldiamines (and catalysts thereof) providing economic and scale-up advantages for commercial-scale applicability due in-part to the reduction or elimination of column chromatography used in the syntheses of the quinolinyldiamines and or intermediates thereof.

For the purposes of the present disclosure, the numbering scheme for the Periodic Table Groups is used as described in *Chemical and Engineering News*, (1985) v. 63 (5), pg. 27. Therefore, a "group 4 metal" is an element from group 4 of the Periodic Table, e.g., Hf, Ti, or Zr.

The specification describes QDA ligands and furthermore transition metal complexes including such compounds. The term "complex" is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which, without being bound by theory, is believed to create a cation as a result of the removal of an anionic group, often referred to as a leaving group, from the transition metal.

The terms "substituent," "radical," "group," and "moiety" may be used interchangeably.

As used herein, and unless otherwise specified, the term "$C_n$" means hydrocarbon(s) having n carbon atom(s) per molecule, wherein n is a positive integer.

As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

Except with respect to the term "substituted hydrocarbyl," the term "substituted" means that at least one hydrogen atom has been replaced with at least one non-hydrogen group, such as a hydrocarbyl group, a heteroatom, or a heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SiR*$_3$, —GeR*$_3$, —SnR*$_3$, —PbR*$_3$, and the like, where each R* is independently a hydrocarbyl or halocarbyl radical, and two or more R* may join together to form a substituted or unsubstituted completely saturated, partially unsaturated, or aromatic cyclic or polycyclic ring structure, or where at least one heteroatom has been inserted within a hydrocarbyl ring. As examples, methyl cyclopentadiene (Cp) is a Cp group substituted with a methyl group, and ethyl alcohol is an ethyl group substituted with an —OH group. The term "substituted hydrocarbyl" means hydrocarbyl radicals in which at least one hydrogen atom of the hydrocarbyl radical has been substituted with a heteroatom or heteroatom-containing group, such as halogen (e.g., Br, Cl, F or I), or at least one functional group such as —NR*$_2$, —OR*, —SeR*, —TeR*, —PR*$_2$, —AsR*$_2$, —SbR*$_2$, —SR*, —BR*$_2$, —SiR*$_3$, —GeR*$_3$, —SnR*$_3$, —PbR*$_3$, and the like, where each R* is independently a hydrocarbyl or halocarbyl radical, and two or more R* may join together to form a substituted or unsubstituted completely saturated, partially unsaturated, or aromatic cyclic or polycyclic ring structure, or where at least one heteroatom has been inserted within a hydrocarbyl ring.

The terms "hydrocarbyl radical," "hydrocarbyl," and "hydrocarbyl group" may be used interchangeably. Likewise, the terms "group," "radical," and "substituent" are also used interchangeably. For purposes of this disclosure, "hydrocarbyl radical" is defined to be $C_1$-$C_{100}$ radicals, that may be linear, branched, or cyclic, and when cyclic, aromatic or non-aromatic. Examples of such radicals can include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like including their substituted analogues.

The terms "alkyl radical," and "alkyl" are used interchangeably. For purposes of this disclosure, "alkyl radical" is defined to be $C_1$-$C_{100}$ alkyls that may be linear, branched, or cyclic. Examples of such radicals can include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like including their substituted analogues. Substituted alkyl radicals are radicals in which at least one hydrogen atom of the alkyl radical has been substituted with at least a non-hydrogen group, such as a hydrocarbyl group, a heteroatom, or a heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SIR*, —SiR*$_3$, —GeR*, —GeR*$_3$, —SnR*, —SnR*$_3$, —PbR*$_3$, and the like, or where at least one heteroatom has been inserted within a hydrocarbyl ring.

The term "alkenyl" means a straight-chain, branched-chain, or cyclic hydrocarbon radical having one or more double bonds. These alkenyl radicals may be optionally substituted. Examples of suitable alkenyl radicals can include ethenyl, propenyl, allyl, 1,4-butadienyl cyclopropenyl, cyclobutenyl, cyclopentenyl, cyclohexenyl, cyclooctenyl, and the like, including their substituted analogues.

The term "alkoxy" or "alkoxide" means an alkyl ether or aryl ether radical where the term alkyl is as defined above. For purposes of the present disclosure, "alkoxides" include those where the alkyl group is a $C_1$ to $C_{10}$ hydrocarbyl. The alkyl group may be straight chain, branched, or cyclic. The alkyl group may be saturated or unsaturated. In some embodiments, the alkyl group may include at least one aromatic group. Examples of suitable alkyl ether radicals can include methoxy, ethoxy, n-propoxy, iso-propoxy, n-butoxy, iso-butoxy, sec-butoxy, tert-butoxy, phenoxyl, and the like.

The term "aryl" or "aryl group" means a carbon-based aromatic ring (e.g. phenyl) and the substituted variants (e.g. 2-methylphenyl, xylyl, 4-bromoxylyl) and polycyclic fused variants (e.g. naphthalenyl, anthracenyl, 2-methylnaphthalenyl). Likewise, heteroaryl means an aryl group where a ring carbon atom (or two or three ring carbon atoms) has been replaced with a heteroatom, such as N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

Where isomers of a named alkyl, alkenyl, alkoxide, or aryl group exist (e.g., n-butyl, iso-butyl, sec-butyl, and tert-butyl) reference to one member of the group (e.g., n-butyl) shall expressly disclose the remaining isomers (e.g., iso-butyl, sec-butyl, and tert-butyl) in the family. Likewise, reference to an alkyl, alkenyl, alkoxide, or aryl group without specifying a particular isomer (e.g., butyl) expressly discloses all isomers (e.g., n-butyl, iso-butyl, sec-butyl, and tert-butyl).

The term "ring atom" means an atom that is part of a cyclic ring structure. By this definition, a benzyl group has six ring atoms and tetrahydrofuran has 5 ring atoms.

The term "saturated" refers to the lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, allyl, acetylide, oxazolinyl, cyclohexenyl, acetyl and the like, and includes alkenyl and alkynyl groups, as well as groups in which double bonds are delocalized, as in aryl and heteroaryl groups as defined below.

The terms "cyclo" and "cyclic" are used herein to refer to saturated or unsaturated radicals containing a single ring or multiple condensed rings. Suitable cyclic moieties include, for example, cyclopentyl, cyclohexyl, cyclooctenyl, bicyclooctyl, phenyl, naphthyl, pyrrolyl, furyl, thiophenyl, imidazolyl, and the like. In at least one embodiment, cyclic moieties include between 3 atoms and 200 atoms other than hydrogen, between 3 atoms and 50 atoms other than hydrogen or between 3 atoms and 20 atoms other than hydrogen.

Throughout the instant specification, certain abbreviations may be used to for the sake of brevity, referring to specific compounds or elements, and include but are not limited to, "i-Pr" to refer to isopropyl; "t-Bu" to refer to tertiary-butyl; "i-Bu" to refer to isobutyl; "Me" to refer to methyl; "Et" to refer to ethyl; "Pr" to refer to propyl, "Bu" to refer to butyl, Ph" to refer to phenyl, "Ind" to refer to indenyl, "Mes" to refer to mesityl (2,4,6-trimethyl phenyl); "TFA" to refer to trifluoroacetate; "d" to refer to day(s); "min" to refer to minute(s); "THF" to refer to tetrahydrofuran; "TsOH" to refer to para-toluenesulfonic acid; "cat." to refer to catalytic amount of; "DMF" to refer to dimethylformamide; "DCM" to refer to dichloromethane; "NBS" to refer to N-bromosuccinimide, "MeOH" to refer to methanol; "eq." to refer to molar equivalents; "rt" or "r.t." to refer to room temperature which is approximately 23° C.; "TMA" to refer to AlMe₃; "TBDMS" to refer to tert-butyl-dimethylsilyl; and the like. Abbreviations for atoms are as given in the periodic table (Li=lithium, for example).

Where isomers of a named alkyl, alkenyl, alkoxide, or aryl group exist (e.g., n-butyl, iso-butyl, sec-butyl, and tert-butyl) reference to one member of the group (e.g., n-butyl) shall expressly disclose the remaining isomers (e.g., iso-butyl, sec-butyl, and tert-butyl) in the family. Likewise, reference to an alkyl, alkenyl, alkoxide, or aryl group without specifying a particular isomer (e.g., butyl) expressly discloses all isomers (e.g., n-butyl, iso-butyl, sec-butyl, and tert-butyl).

The terms "halo" and "halogen" refer to a chloro, bromo, fluoro or iodo radical.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom-substituted ring. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, and isoquinolinyl.

The term "heteroaryl" refers to an aryl radical that includes one or more heteroatoms in the aromatic ring. Examples of heteroaryl groups include groups containing heteroaromatic rings such as quinolinyl, thiophene, pyridine, pyrazine, isoxazole, pyrazole, pyrrole, furan, thiazole, oxazole, imidazole, isothiazole, oxadiazole, triazole, and benzo-fused analogues of these rings, such as indole, carbazole, benzofuran, benzothiophene, and the like.

The term "quinolinyl", as used herein, refers to a substituted or unsubstituted group represented by the structure:

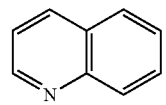

A "catalyst system" includes at least one catalyst compound and at least one activator. When "catalyst system" is used to describe such the catalyst compound/activator combination before activation, it means the unactivated catalyst complex (precatalyst) together with an activator and, optionally, a co-activator. When it is used to describe the combination after activation, it means the activated complex and the activator or other charge-balancing moiety. The transition metal compound may be neutral as in a precatalyst, or a charged species with a counter ion as in an activated catalyst system.

As used herein, "column chromatography" is the commonly used method to purify and isolate a single chemical compound from a mixture of compounds that involves the adsorption of the mixture on a stationary phase, such as silica gel or alumina, followed by elution with solvent(s). The general method is described in the following references: Bobbitt, J. M. et al. (1968) *Introduction to Chromatography*, Reinhold, New York; Stock R. et al. (1967) *Chromatographic Methods*, 2$^{nd}$ ed., Chapman and Hall, London; Gordon A. J. et al. (1972) *The Chemist's Companion: A Handbook of Practical Data, Techniques, and References*, John Wiley & Sons, New York.

In the description herein, the catalyst may be described as a catalyst precursor, a precatalyst compound, catalyst compound or a transition metal compound, and these terms are used interchangeably. A polymerization catalyst system is a catalyst system that can polymerize monomers to polymer. An "anionic ligand" is a negatively charged ligand which donates one or more pairs of electrons to a metal ion. A "neutral donor ligand" is a neutrally charged ligand which donates one or more pairs of electrons to a metal ion.

Ligand Compounds

The present disclosure relates to quinolinyldiamine compounds where a three-atom linker, can be used between the quinoline and the nitrogen donor in the 2-position of the quinoline ring, important aspect for making catalyst complexes. Indeed, upon deprotonation and coordination of the quinolinyldiamino ligand to a transition metal the use of a three-atom linker yields a metal complex with a seven-membered chelate ring that is not coplanar with the other five-membered chelate ring. The resulting complex is thought to be effectively chiral ($C_1$ symmetry), even when there are no permanent stereo-centers present. This is a desirable catalyst feature, for example, for the production of isotactic polyolefins.

A QDA compound can be represented by Formula (I):

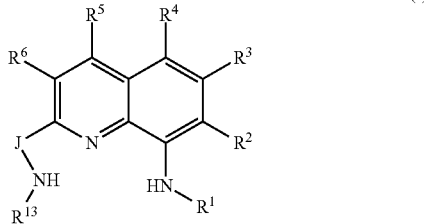

(I)

wherein:
J is group including a three-atom-length bridge between the quinoline and the amine nitrogen, such as a group containing up to 50 non-hydrogen atoms;
$R^1$ and $R^{13}$ are independently selected from hydrocarbyl, substituted hydrocarbyl, and silyl groups;
$R^2$, $R^3$, $R^4$, $R^5$, and $R^6$ are independently hydrogen, hydrocarbyl, alkoxy, silyl, amino, aryloxy, substituted hydrocarbyl, halogen, or phosphino.

A QDA compound can be represented by Formula (II):

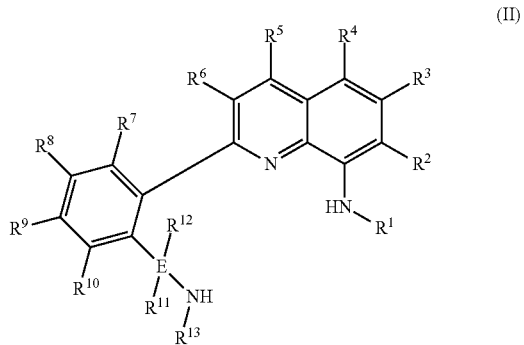

(II)

wherein:
E is carbon, silicon, or germanium;
$R^1$ and $R^{13}$ are independently selected from hydrocarbyl, substituted hydrocarbyl, and silyl groups;
$R^2$, $R^3$, $R^4$, $R^5$, $R^6$, $R^7$, $R^8$, $R^9$, $R^{10}$, $R^{11}$, $R^{12}$, and $R^{14}$ are independently hydrogen, hydrocarbyl, alkoxy, silyl, amino, aryloxy, substituted hydrocarbyl, halogen, or phosphino.

A QDA compound can be represented by Formula (III):

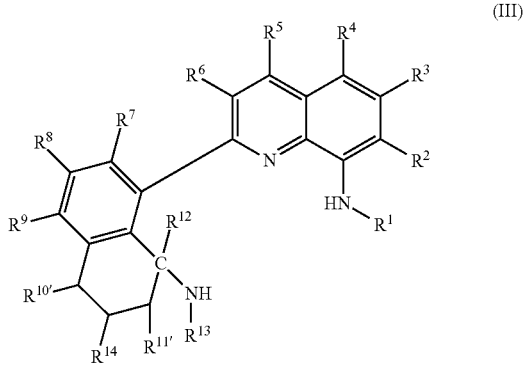

(III)

wherein:
$R^1$ and $R^{13}$ are independently selected from hydrocarbyl, substituted hydrocarbyl, and silyl groups;
$R^2$, $R^3$, $R^4$, $R^5$, $R^6$, $R^7$, $R^8$, $R^9$, $R^{10}$, $R^{10'}$, $R^{11}$, $R^{11'}$, $R^{12}$, and $R^{14}$ are independently hydrogen, hydrocarbyl, alkoxy, silyl, amino, aryloxy, substituted hydrocarbyl, halogen, or phosphino.

In at least one embodiment, any two adjacent R groups (e.g., $R^1$ & $R^2$, $R^2$ & $R^3$, $R^{10}$ and $R^{11}$, etc.) may be joined to form a substituted hydrocarbyl, unsubstituted hydrocarbyl, substituted heterocyclic, or unsubstituted heterocyclic, saturated or unsaturated ring, where the ring has 5, 6, 7, or 8 ring atoms and where substitutions on the ring can join to form additional rings.

In at least one embodiment of Formula (I), J is an aromatic substituted or unsubstituted hydrocarbyl (such as a hydrocarbyl) having from 3 to 30 non-hydrogen atoms, such as J is represented by the formula:

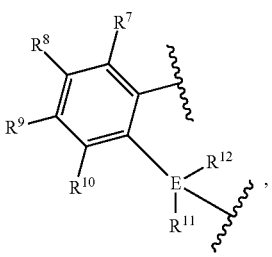

such as J is

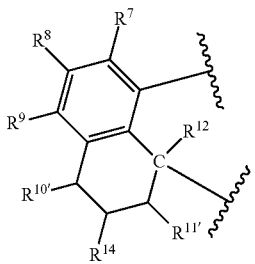

where $R^7$, $R^8$, $R^9$, $R^{10}$, $R^{10'}$, $R^{11}$, $R^{11'}$, $R^{12}$, $R^{14}$ and E are as defined above, and any two R groups (e.g., $R^7$ & $R^8$, $R^8$ & $R^9$, $R^9$ & $R^{10}$, $R^{10}$ & $R^{11}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated or aromatic), such as J is an arylalkyl (such as arylmethyl, etc.) or dihydro-1H-indenyl, or tetrahydronaphthalenyl group, where ⸳⸳ indicates connection to the ligand compound.

In at least one embodiment of Formula (I), J is selected from the following structures:

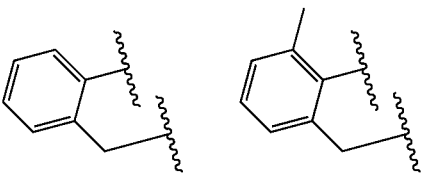

-continued

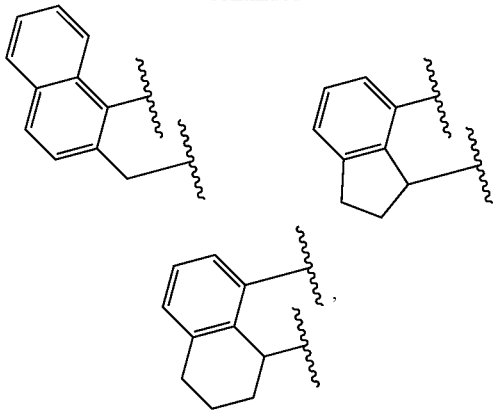

where ⌇ indicates connection to the ligand compound.

In at least one embodiment of Formula (II), E is carbon.

In at least one embodiment of Formulas (II) or (III), $R^7$ and $R^8$ are joined to form a six-membered aromatic ring with the joined $R^7R^8$ group being —CH=CHCH=CH—.

In at least one embodiment of Formulas (I), (II), or (III), $R^{10}$ and $R^{11}$ are joined to form a five-membered ring with the joined $R^{10}R^{11}$ group being —CH$_2$CH$_2$—.

In at least one embodiment of Formulas (I), (II), or (III), $R^{10}$ and $R^{11}$ are joined to form a six-membered ring with the joined $R^{10}R^{11}$ group being —CH$_2$CH$_2$CH$_2$—.

In at least one embodiment of Formulas (I), (II), or (III), $R^1$ and $R^{13}$ are independently selected from phenyl groups that are variously substituted with between zero to five substituents that include F, Cl, Br, I, CF$_3$, NO$_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In at least one embodiment, the QDA is represented by Formula (II) above where: E is selected from carbon, silicon, or germanium (such as carbon); $R^1$ and $R^{13}$ are independently selected from hydrocarbyl, substituted hydrocarbyl, and silyl groups (such as aryl); $R^2$, $R^3$, $R^4$, $R^5$, $R^6$, $R^7$, $R^8$, $R^9$, $R^{10}$, $R^{11}$, and $R^{12}$ are independently hydrogen, hydrocarbyl, alkoxy, silyl, amino, aryloxy, substituted hydrocarbyls, halogen, and phosphino; $R^7$ and $R^8$ may be joined to form a ring (such as an aromatic ring, a six-membered aromatic ring with the joined $R^7R^8$ group being —CH=CHCH=CH—); $R^{10}$ and $R^{11}$ may be joined to form a ring (such as a five-membered ring with the joined $R^{10}R^{11}$ group being —CH$_2$CH$_2$—, a six-membered ring with the joined $R^{10}R^{11}$ group being —CH$_2$CH$_2$CH$_2$—).

In at least one embodiment of Formulas (I), (II), or (III), $R^4$, $R^5$, and $R^6$ are independently selected from hydrogen, hydrocarbyl, substituted hydrocarbyl, alkoxy, aryloxy, halogen, amino, and silyl, and wherein adjacent R groups ($R^4$ and $R^5$ and/or $R^5$ and $R^6$) may be joined to form a substituted hydrocarbyl, unsubstituted hydrocarbyl, unsubstituted heterocyclic ring or substituted heterocyclic ring, where the ring has 5, 6, 7, or 8 ring atoms and where substitutions on the ring can join to form additional rings.

In at least one embodiment of Formulas (I), (II), or (III), $R^7$, $R^8$, $R^9$, and $R^{10}$ are independently selected from hydrogen, hydrocarbyl, substituted hydrocarbyl, alkoxy, halogen, amino, and silyl, and wherein adjacent R groups ($R^7$ and $R^8$ and/or $R^9$ and $R^{10}$) may be joined to form a saturated, substituted hydrocarbyl, unsubstituted hydrocarbyl, unsubstituted heterocyclic ring or substituted heterocyclic ring, where the ring has 5, 6, 7, or 8 ring carbon atoms and where substitutions on the ring can join to form additional rings.

In at least one embodiment of Formulas (I), (II), or (III), $R^2$ and $R^3$ are each, independently, selected from hydrogen, hydrocarbyl, substituted hydrocarbyl, alkoxy, silyl, amino, aryloxy, halogen, and phosphino, $R^2$ and $R^3$ may be joined to form a saturated, substituted or unsubstituted hydrocarbyl ring, where the ring has 4, 5, 6, or 7 ring carbon atoms and where substitutions on the ring can join to form additional rings, or $R^2$ and $R^3$ may be joined to form a saturated heterocyclic ring, or a saturated substituted heterocyclic ring where substitutions on the ring can join to form additional rings.

In at least one embodiment of Formulas (I), (II), or (III), $R^{11}$ and $R^{12}$ are each, independently, selected from hydrogen, hydrocarbyl, substituted hydrocarbyl, alkoxy, silyl, amino, aryloxy, halogen, and phosphino, $R^{11}$ and $R^{12}$ may be joined to form a saturated, substituted or unsubstituted hydrocarbyl ring, where the ring has 4, 5, 6, or 7 ring carbon atoms and where substitutions on the ring can join to form additional rings, or $R^{11}$ and $R^{12}$ may be joined to form a saturated heterocyclic ring, or a saturated substituted heterocyclic ring where substitutions on the ring can join to form additional rings, or $R^{11}$ and $R^{10}$ may be joined to form a saturated heterocyclic ring, or a saturated substituted heterocyclic ring where substitutions on the ring can join to form additional rings.

In at least one embodiment of Formulas (I), (II), or (III), $R^1$ and $R^{13}$ are independently selected from phenyl groups that are variously substituted with between zero to five substituents that include F, Cl, Br, I, CF$_3$, NO$_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In at least one embodiment of Formula (II), suitable $R^{12}$-E-$R^{11}$ groups include CH$_2$, CMe$_2$, SiMe$_2$, SiEt$_2$, SiPr$_2$, SiBu$_2$, SiPh$_2$, Si(aryl)$_2$, Si(alkyl)$_2$, CH(aryl), CH(Ph), CH(alkyl), and CH(2-isopropylphenyl), where alkyl is a C$_1$ to C$_{40}$ alkyl group (such as C$_1$ to C$_{20}$ alkyl, such as one or more of methyl, ethyl, propyl, butyl, pentyl, hexyl, heptyl, octyl, nonyl, decyl, undecyl, dodecyl, and isomers thereof), aryl is a C$_5$ to C$_{40}$ aryl group (such as a C$_6$ to C$_{20}$ aryl group, such as phenyl or substituted phenyl, such as phenyl, 2-isopropylphenyl, or 2-tertbutylphenyl).

In at least one embodiment of Formula (III), $R^9$, $R^{10}$, $R^{11}$, $R^{12}$, $R^{14}$, and are independently selected from hydrogen, hydrocarbyl, substituted hydrocarbyl, alkoxy, halogen, amino, and silyl, and wherein adjacent R groups ($R^{10}$ and $R^{14}$, and/or $R^{11}$ and $R^{14}$, and/or $R^9$ and $R^{10}$) may be joined to form a saturated, substituted hydrocarbyl, unsubstituted hydrocarbyl, unsubstituted heterocyclic ring or substituted heterocyclic ring, where the ring has 5, 6, 7, or 8 ring carbon atoms and where substitutions on the ring can join to form additional rings.

In at least one embodiment of Formulas (I), (II), or (III), the R groups above (i.e., any of $R^2$ to $R^{14}$) and other R groups mentioned hereafter, contain from 1 to 30, such as 2 to 20 carbon atoms, especially from 6 to 20 carbon atoms. Suitable R groups above (i.e., any of $R^2$ to $R^{14}$) and other R groups mentioned hereafter can be independently selected from hydrogen, methyl, ethyl, phenyl, isopropyl, isobutyl, trimethylsilyl, and —CH$_2$—Si(Me)$_3$.

In at least one embodiment of Formula (II), E is carbon and $R^{11}$ and $R^{12}$ are independently selected from phenyl groups that are substituted with 0, 1, 2, 3, 4, or 5 substituents selected from F, Cl, Br, I, CF$_3$, NO$_2$, alkoxy, dialkylamino, hydrocarbyl, and substituted hydrocarbyl groups with from one to ten carbons.

In at least one embodiment of Formula (II) or (III), R$^{11}$ and R$^{12}$ are independently selected from hydrogen, methyl, ethyl, phenyl, isopropyl, isobutyl, —CH$_2$—Si(Me)$_3$, and trimethylsilyl.

In at least one embodiment of Formula (II) or (III), R$^7$, R$^8$, R$^9$, and R$^{10}$ are independently selected from hydrogen, methyl, ethyl, propyl, isopropyl, phenyl, cyclohexyl, fluoro, chloro, methoxy, ethoxy, phenoxy, —CH$_2$—Si(Me)$_3$, and trimethylsilyl.

In at least one embodiment of Formula (I), (II) or (III), R$^2$, R$^3$, R$^4$, R$^5$, and R$^6$ are independently selected from hydrogen, hydrocarbyl, alkoxy, silyl, amino, substituted hydrocarbyl, and halogen.

In at least one embodiment of Formula (III), R$^{10}$, R$^{11}$ and R$^{14}$ are independently selected from hydrogen, methyl, ethyl, phenyl, isopropyl, isobutyl, —CH$_2$—Si(Me)$_3$, and trimethylsilyl.

In at least one embodiment of Formula (I), (II) or (III), R$^1$ is 2,6-diisopropylphenyl, 2,4,6-triisopropylphenyl, 2,6-diisopropyl-4-methylphenyl, 2,6-diethylphenyl, 2-ethyl-6-isopropylphenyl, 2,6-bis(3-pentyl)phenyl, 2,6-dicyclopentylphenyl, or 2,6-dicyclohexylphenyl.

In at least one embodiment of Formula (I), (II), and (III), R$^{13}$ is phenyl, 2-methylphenyl, 2-ethylphenyl, 2-propylphenyl, 2,6-dimethylphenyl, 2-isopropylphenyl, 4-methylphenyl, 3,5-dimethylphenyl, 3,5-di-tert-butylphenyl, 4-fluorophenyl, 3-methylphenyl, 4-dimethylaminophenyl, or 2-phenylphenyl.

In at least one embodiment of Formula (II), J is dihydro-1H-indenyl and R$^1$ is 2,6-dialkylphenyl or 2,4,6-trialkylphenyl.

In at least one embodiment of Formula (I), (II) or (III), R$^1$ is 2,6-diisopropylphenyl and R$^{13}$ is a hydrocarbyl group containing 1, 2, 3, 4, 5, 6, or 7 carbon atoms.

In at least one embodiment of Formula (I), R$^1$ is a diisopropylphenyl group and R$^2$, R$^3$, R$^4$, R$^5$, R$^6$ are independently hydrogen, R$^{13}$ is a phenyl and J is represented by the following structure:

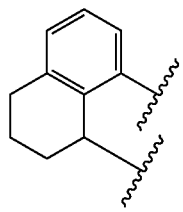 [SMILES: *c1cccc2c1C(*)CCC2]

where ⸘ indicates connection to the compound.

In an alternate embodiment of Formula (I), (II) or (III), R$^1$ is a 4-hexylphenyl group and R$^2$, R$^3$, R$^4$, R$^5$, R$^6$ are independently hydrogen.

In an alternate embodiment of Formula (I), R$^1$ independently selected from hydrocarbyl, substituted hydrocarbyl, and silyl groups, and R$^2$, R$^3$, R$^4$, R$^5$, R$^6$ are independently hydrogen, and J is represented by the following structure:

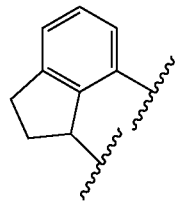 [SMILES: *c1cccc2c1C(*)CC2]

where ⸘ indicates connection to the compound.

In an alternate embodiment of Formula (I), J is represented by the following formula:

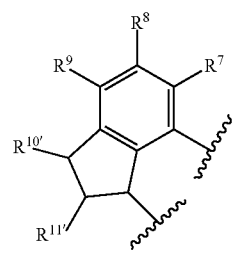

where R$^2$, R$^3$, R$^4$, R$^5$, R$^6$, R$^7$, R$^8$, R$^9$, R$^{10'}$, and R$^{11'}$ are independently hydrogen, hydrocarbyl, alkoxy, silyl, amino, aryloxy, substituted hydrocarbyl, halogen, or phosphino, or any two R groups (e.g., R$^7$ & R$^8$, R$^8$ & R$^9$, R$^9$ & R$^{10'}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated ⸘ or aromatic), and where ⸘ indicates connection to the ligand.

In at least one embodiment, the ligand compound represented by Formula (I) is:

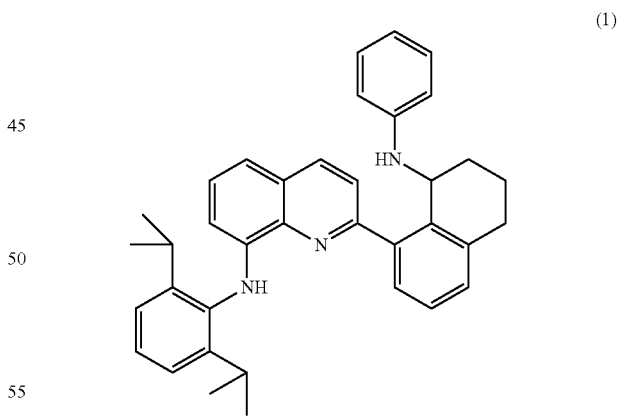

(1)

2-(8-Anilino-5,6,7,8-tetrahydronaphthalen-1-yl)-N-(2,6-diisopropylphenyl)quinolin-8-amine.

In another aspect of the present disclosure, various processes for synthesizing QDA intermediates, ligands, and catalyst complexes are described herein.

Catalyst Compounds

The present disclosure relates to making quinolinyldiamido transition metal complexes. Quinolinyldiamido transition metal complexes are catalyst complexes where a three-atom linker is used between the quinoline and the nitrogen donor in the 2-position of the quinoline ring. The has been found to be an important aspect because the use of the three-atom linker is believed to yield a metal complex with a seven-membered chelate ring that is not coplanar with the other five-membered chelate ring. The resulting complex is thought to be effectively chiral ($C_1$ symmetry), even when there are no permanent stereo-centers present. This is a desirable catalyst feature, for example, for the production of isotactic polyolefins.

A quinolinyldiamido transition metal complex may be represented by Formula (IV):

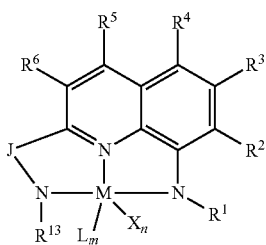

(IV)

wherein:

M is a Group 3, 4, 5, 6, 7, 8, 9, 10, 11, or 12 metal (such as a group 4 metal);

J is group including a three-atom-length bridge between the quinoline and the amido nitrogen, such as a group containing up to 50 non-hydrogen atoms;

E is carbon, silicon, or germanium;

X is an anionic leaving group, (such as a hydrocarbyl group or a halogen);

L is a neutral Lewis base;

$R^1$ and $R^{13}$ are independently selected from hydrocarbyl, substituted hydrocarbyl, and silyl groups;

$R^2$, $R^3$, $R^4$, $R^5$, and $R^6$ are independently hydrogen, hydrocarbyl, alkoxy, silyl, amino, aryloxy, substituted hydrocarbyl, halogen, or phosphino;

n is 1 or 2;

m is 0, 1, or 2, where n+m is not greater than 4; and any two R groups (e.g., $R^1$ & $R^2$, $R^2$ & $R^3$, etc.) may be joined to form a substituted hydrocarbyl, unsubstituted hydrocarbyl, substituted heterocyclic, or unsubstituted heterocyclic, saturated or unsaturated ring, where the ring has 5, 6, 7, or 8 ring atoms and where substitutions on the ring can join to form additional rings;

any two X groups may be joined together to form a dianionic group;

any two L groups may be joined together to form a bidentate Lewis base; and any X group may be joined to an L group to form a monoanionic bidentate group.

A quinolinyldiamido transition metal complex may be represented by Formula (V):

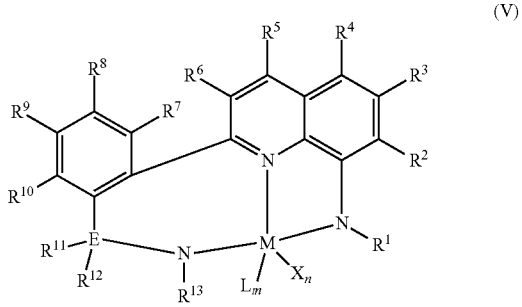

(V)

wherein:

M is a Group 3, 4, 5, 6, 7, 8, 9, 10, 11, or 12 metal (such as a group 4 metal);

E is carbon, silicon, or germanium;

X is an anionic leaving group, (such as a hydrocarbyl group or a halogen);

L is a neutral Lewis base;

$R^1$ and $R^{13}$ are independently selected from hydrocarbyl, substituted hydrocarbyl, and silyl groups;

$R^2$, $R^3$, $R^4$, $R^5$, $R^6$, $R^7$, $R^8$, $R^9$, $R^{10}$, $R^{11}$, and $R^{12}$ are independently hydrogen, hydrocarbyl, alkoxy, silyl, amino, aryloxy, substituted hydrocarbyl, halogen, or phosphino;

n is 1 or 2;

m is 0, 1, or 2, where n+m is not greater than 4; and any two R groups (e.g., $R^1$ & $R^2$, $R^2$ & $R^3$, $R^{10}$ and $R^{11}$, etc.) may be joined to form a substituted hydrocarbyl, unsubstituted hydrocarbyl, substituted heterocyclic, or unsubstituted heterocyclic, saturated or unsaturated ring, where the ring has 5, 6, 7, or 8 ring atoms and where substitutions on the ring can join to form additional rings;

any two X groups may be joined together to form a dianionic group;

any two L groups may be joined together to form a bidentate Lewis base; and any X group may be joined to an L group to form a monoanionic bidentate group.

A quinolinyldiamido transition metal complex may be represented by Formula (VI):

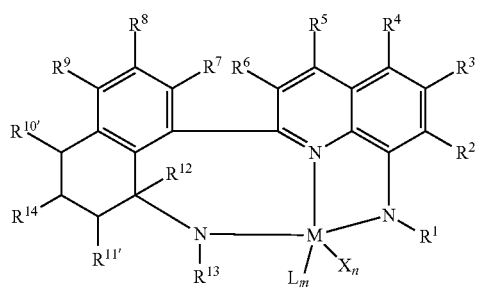

(VI)

wherein:

M is a Group 3, 4, 5, 6, 7, 8, 9, 10, 11, or 12 metal (such as a group 4 metal);

X is an anionic leaving group, (such as a hydrocarbyl group or a halogen);

L is a neutral Lewis base;

$R^1$ and $R^{13}$ are independently selected from hydrocarbyl, substituted hydrocarbyl, and silyl groups;

$R^2$, $R^3$, $R^4$, $R^5$, $R^6$, $R^7$, $R^8$, $R^9$, $R^{10'}$, $R^{11'}$, $R^{12}$, and $R^{14}$ are independently hydrogen, hydrocarbyl, alkoxy, silyl, amino, aryloxy, substituted hydrocarbyl, halogen, or phosphino;

n is 1 or 2;

m is 0, 1, or 2, where n+m is not greater than 4; and any two R groups (e.g., $R^1$ & $R^2$, $R^2$ & $R^3$, etc.) may be joined to form a substituted hydrocarbyl, unsubstituted hydrocarbyl, substituted heterocyclic, or unsubstituted heterocyclic, saturated or unsaturated ring, where the ring has 5, 6, 7, or 8 ring atoms and where substitutions on the ring can join to form additional rings;

any two X groups may be joined together to form a dianionic group;

any two L groups may be joined together to form a bidentate Lewis base; and any X group may be joined to an L group to form a monoanionic bidentate group.

In at least one embodiment of Formulas (IV), (V), or (VI), M is a Group 4 metal, such as zirconium or hafnium.

In at least one embodiment of Formula (IV), J is an aromatic substituted or unsubstituted hydrocarbyl (such as a hydrocarbyl) having from 3 to 30 non-hydrogen atoms, such as J is represented by the formula:

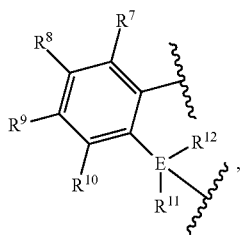

such as J is

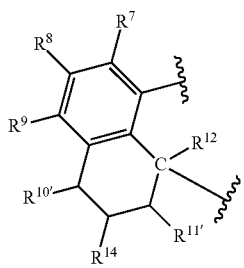

where $R^7$, $R^8$, $R^9$, $R^{10}$, $R^{10'}$, $R^{11}$, $R^{11'}$, $R^{12}$, $R^{14}$ and E are as defined above, and any two R groups (e.g., $R^7$ & $R^8$, $R^8$ & $R^9$, $R^9$ & $R^{10}$, $R^{10}$ & $R^{11}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated or aromatic), such as J is an arylalkyl (such as arylmethyl, etc.) or dihydro-1H-indenyl, or tetrahydronaphthalenyl group.

In at least one embodiment of Formula (IV), J is selected from the following structures:

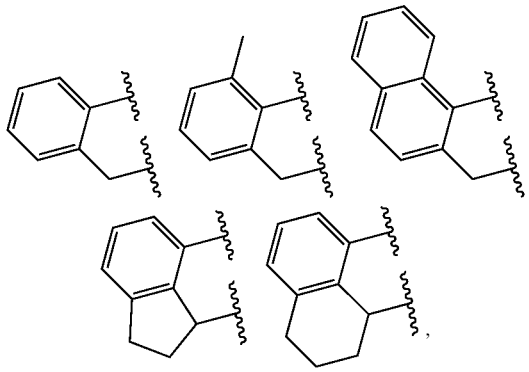

where ⸾ indicates connection to the complex.

In an alternate embodiment of Formula (IV), J is represented by the following formula:

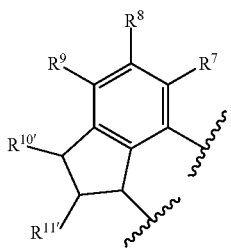

where $R^2$, $R^3$, $R^4$, $R^5$, $R^6$, $R^7$, $R^8$, $R^9$, $R^{10'}$, and $R^{11'}$ are independently hydrogen, hydrocarbyl, alkoxy, silyl, amino, aryloxy, substituted hydrocarbyl, halogen, or phosphino, or any two R groups (e.g., $R^7$ & $R^8$, $R^8$ & $R^9$, $R^9$ & $R^{10'}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated or aromatic), and where ⸾ indicates connection to the complex.

In at least one embodiment of Formula (V), E is carbon.

In at least one embodiment of Formulas (IV), (V), or (VI), X is alkyl (such as alkyl groups having 1 to 10 carbons, such as methyl, ethyl, propyl, butyl, pentyl, hexyl, heptyl, octyl, nonyl, decyl, and isomers thereof), aryl, hydride, alkylsilane, fluoride, chloride, bromide, iodide, triflate, carboxylate, amido (such as NMe$_2$), or alkylsulfonate.

In at least one embodiment of Formulas (IV), (V), or (VI), L is an ether, amine or thioether.

In at least one embodiment of Formulas (V) or (VI), $R^7$ and $R^8$ are joined to form a six-membered aromatic ring with the joined $R^7R^8$ group being —CH=CHCH=CH—.

In at least one embodiment of Formula (V), $R^{10}$ and $R^{11}$ are joined to form a five-membered ring with the joined $R^{1'}R^{11}$ group being —CH$_2$CH$_2$—.

In at least one embodiment of Formula (V), $R^{10}$ and $R^{11}$ are joined to form a six-membered ring with the joined $R^{10}R^{11}$ group being —CH$_2$CH$_2$CH$_2$—.

In at least one embodiment of Formulas (IV), (V), or (VI), $R^1$ and $R^{13}$ may be independently selected from phenyl groups that are variously substituted with between zero to five substituents that include F, Cl, Br, I, CF$_3$, NO$_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In at least one embodiment, the quinolinyldiamido transition metal complex represented by the Formula (V) above where:

M is a Group 4 metal (such as hafnium);

E is selected from carbon, silicon, or germanium (such as carbon);

X is an alkyl, aryl, hydride, alkylsilane, fluoride, chloride, bromide, iodide, triflate, carboxylate, amido, alkoxo, or alkylsulfonate;

L is an ether, amine, or thioether;

$R^1$ and $R^{13}$ are independently selected from hydrocarbyl, substituted hydrocarbyl, and silyl groups (such as aryl);

$R^2$, $R^3$, $R^4$, $R^5$, $R^6$, $R^7$, $R^8$, $R^9$, $R^{10}$, $R^{11}$, and $R^{12}$ are independently hydrogen, hydrocarbyl, alkoxy, silyl, amino, aryloxy, substituted hydrocarbyls, halogen, and phosphino;

n is 1 or 2;

m is 0, 1, or 2;

n+m is from 1 to 4; and two X groups may be joined together to form a dianionic group;

two L groups may be joined together to form a bidentate Lewis base;

an X group may be joined to an L group to form a monoanionic bidentate group;

$R^7$ and $R^8$ may be joined to form a ring (such as an aromatic ring, a six-membered aromatic ring with the joined $R^7R^8$ group being —CH=CHCH=CH—);

$R^{10}$ and $R^{11}$ may be joined to form a ring (such as a five-membered ring with the joined $R^{10}R^{11}$ group being —CH$_2$CH$_2$—, a six-membered ring with the joined $R^{10}R^{11}$ group being —CH$_2$CH$_2$CH$_2$—).

In at least one embodiment of Formulas (IV), (V), or (VI), $R^4$, $R^5$, and $R^6$ are independently selected from hydrogen, hydrocarbyl, substituted hydrocarbyl, alkoxy, aryloxy, halogen, amino, and silyl, and wherein adjacent R groups ($R^4$ and $R^5$ and/or $R^5$ and $R^6$) may be joined to form a substituted hydrocarbyl, unsubstituted hydrocarbyl, unsubstituted heterocyclic ring or substituted heterocyclic ring, where the ring has 5, 6, 7, or 8 ring atoms and where substitutions on the ring can join to form additional rings.

In at least one embodiment of Formulas (IV), (V), or (VI), $R^7$, $R^8$, $R^9$, and $R^{10}$ are independently selected from hydrogen, hydrocarbyl, substituted hydrocarbyl, alkoxy, halogen, amino, and silyl, and wherein adjacent R groups ($R^7$ and $R^8$ and/or $R^9$ and $R^{10}$) may be joined to form a saturated, substituted hydrocarbyl, unsubstituted hydrocarbyl, unsubstituted heterocyclic ring or substituted heterocyclic ring, where the ring has 5, 6, 7, or 8 ring carbon atoms and where substitutions on the ring can join to form additional rings.

In at least one embodiment of Formulas (IV), (V), or (VI), $R^2$ and $R^3$ are each, independently, selected from hydrogen, hydrocarbyl, substituted hydrocarbyl, alkoxy, silyl, amino, aryloxy, halogen, and phosphino, $R^2$ and $R^3$ may be joined to form a saturated, substituted or unsubstituted hydrocarbyl ring, where the ring has 4, 5, 6, or 7 ring carbon atoms and where substitutions on the ring can join to form additional rings, or $R^2$ and $R^3$ may be joined to form a saturated heterocyclic ring, or a saturated substituted heterocyclic ring where substitutions on the ring can join to form additional rings.

In at least one embodiment of Formulas (IV), (V), or (VI), $R^{11}$ and $R^{12}$ are each, independently, selected from hydrogen, hydrocarbyl, substituted hydrocarbyl, alkoxy, silyl, amino, aryloxy, halogen, and phosphino, $R^{11}$ and $R^{12}$ may be joined to form a saturated, substituted or unsubstituted hydrocarbyl ring, where the ring has 4, 5, 6, or 7 ring carbon atoms and where substitutions on the ring can join to form additional rings, or $R^{11}$ and $R^{12}$ may be joined to form a saturated heterocyclic ring, or a saturated substituted heterocyclic ring where substitutions on the ring can join to form additional rings, or $R^{11}$ and $R^{10}$ may be joined to form a saturated heterocyclic ring, or a saturated substituted heterocyclic ring where substitutions on the ring can join to form additional rings.

In at least one embodiment of Formulas (IV), (V), and (VI), $R^1$ and $R^{13}$ may be independently selected from phenyl groups that are variously substituted with between zero to five substituents that include F, Cl, Br, I, CF$_3$, NO$_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In at least one embodiment of Formula (V), suitable $R^{12}$-E-$R^{11}$ groups include CH$_2$, CMe$_2$, SiMe$_2$, SiEt$_2$, SiPr$_2$, SiBu$_2$, SiPh$_2$, Si(aryl)$_2$, Si(alkyl)$_2$, CH(aryl), CH(Ph), CH(alkyl), and CH(2-isopropylphenyl), where alkyl is a C$_1$ to C$_{40}$ alkyl group (such as C$_1$ to C$_{20}$ alkyl, such as one or more of methyl, ethyl, propyl, butyl, pentyl, hexyl, heptyl, octyl, nonyl, decyl, undecyl, dodecyl, and isomers thereof), aryl is a C$_5$ to C$_{40}$ aryl group (such as a C$_6$ to C$_{20}$ aryl group, such as phenyl or substituted phenyl, such as phenyl, 2-isopropylphenyl, or 2-tertbutylphenyl).

In at least one embodiment of Formula (VI), $R^{11}$, $R^{12}$, $R^9$, $R^{14}$, and $R^{10}$ are independently selected from hydrogen, hydrocarbyl, substituted hydrocarbyl, alkoxy, halogen, amino, and silyl, and wherein adjacent R groups ($R^{10}$ and $R^{14}$, and/or $R^{11}$ and $R^{14}$, and/or $R^9$ and $R^{10}$) may be joined to form a saturated, substituted hydrocarbyl, unsubstituted hydrocarbyl, unsubstituted heterocyclic ring or substituted heterocyclic ring, where the ring has 5, 6, 7, or 8 ring carbon atoms and where substitutions on the ring can join to form additional rings.

For example, the R groups above (i.e., any of $R^2$ to $R^{14}$) and other R groups mentioned hereafter, contain from 1 to 30, such as 2 to 20 carbon atoms, such as from 6 to 20 carbon atoms. In at least one embodiment, the R groups above (i.e., any of $R^2$ to $R^{14}$) and other R groups mentioned hereafter, are independently selected from hydrogen, methyl, ethyl, phenyl, isopropyl, isobutyl, trimethylsilyl, and —CH$_2$—Si(Me)$_3$.

In at least one embodiment, the quinolinyldiamido complex is linked to one or more additional transition metal complex, such as a quinolinyldiamido complex or a metallocene, through an R group in such a fashion as to make a bimetallic, trimetallic, or multimetallic complex that may be used as a catalyst component for olefin polymerization. The linker R-group in such a complex may contain 1 to 30 carbon atoms.

In at least one embodiment of Formulas (IV), (V), and (VI), M is Ti, Zr, or Hf, and E is carbon, with Zr or Hf based complexes, such as M is Hf and E is carbon.

In at least one embodiment of the present disclosure, E is carbon and $R^{12}$ and $R^{11}$ are independently selected from phenyl groups that are substituted with 0, 1, 2, 3, 4, or 5 substituents selected from F, Cl, Br, I, CF$_3$, NO$_2$, alkoxy, dialkylamino, hydrocarbyl, and substituted hydrocarbyl groups with from one to ten carbons.

In at least one embodiment of Formulas (V) or (VI), $R^{11}$ and $R^{12}$ are independently selected from hydrogen, methyl, ethyl, phenyl, isopropyl, isobutyl, —CH$_2$—Si(Me)$_3$, and trimethylsilyl.

In at least one embodiment of Formulas (V) or (VI), $R^7$, $R^8$, $R^9$, and $R^{10}$ are independently selected from hydrogen, methyl, ethyl, propyl, isopropyl, phenyl, cyclohexyl, fluoro, chloro, methoxy, ethoxy, phenoxy, —CH$_2$—Si(Me)$_3$, and trimethylsilyl.

In at least one embodiment of Formulas (IV), (V), or (VI), R$^2$, R$^3$, R$^4$, R$^5$, and R$^6$ are independently selected from hydrogen, hydrocarbyl, alkoxy, silyl, amino, substituted hydrocarbyl, and halogen.

In at least one embodiment of Formula (VI), R$^{10}$, R$^{11}$ and R$^{14}$ are independently selected from hydrogen, methyl, ethyl, phenyl, isopropyl, isobutyl, —CH$_2$—Si(Me)$_3$, and trimethylsilyl.

In at least one embodiment of Formulas (IV), (V), or (VI), each L is independently selected from Et$_2$O, MeOtBu, Et$_3$N, PhNMe$_2$, MePh$_2$N, tetrahydrofuran, and dimethylsulfide.

In at least one embodiment of Formula (IV), (V), and (VI), each X is independently selected from methyl, benzyl, trimethylsilyl, neopentyl, ethyl, propyl, butyl, phenyl, hydrido, chloro, fluoro, bromo, iodo, dimethylamido, diethylamido, dipropylamido, and diisopropylamido.

In at least one embodiment of Formulas (IV), (V), or (VI), R$^1$ is 2,6-diisopropylphenyl, 2,4,6-triisopropylphenyl, 2,6-diisopropyl-4-methylphenyl, 2,6-diethylphenyl, 2-ethyl-6-isopropylphenyl, 2,6-bis(3-pentyl)phenyl, 2,6-dicyclopentylphenyl, or 2,6-dicyclohexylphenyl.

In at least one embodiment of Formulas (IV), (V), or (VI), R$^{13}$ is phenyl, 2-methylphenyl, 2-ethylphenyl, 2-propylphenyl, 2,6-dimethylphenyl, 2-isopropylphenyl, 4-methylphenyl, 3,5-dimethylphenyl, 3,5-di-tert-butylphenyl, 4-fluorophenyl, 3-methylphenyl, 4-dimethylaminophenyl, or 2-phenylphenyl.

In at least one embodiment of Formula (V), J is dihydro-1H-indenyl and R$^1$ is 2,6-dialkylphenyl or 2,4,6-trialkylphenyl.

In at least one embodiment of Formulas (IV), (V), or (VI), R$^1$ is 2,6-diisopropylphenyl and R$^{13}$ is a hydrocarbyl group containing 1, 2, 3, 4, 5, 6, or 7 carbon atoms.

In at least one embodiment, the ligand compound represented by formula (IV) is selected from:

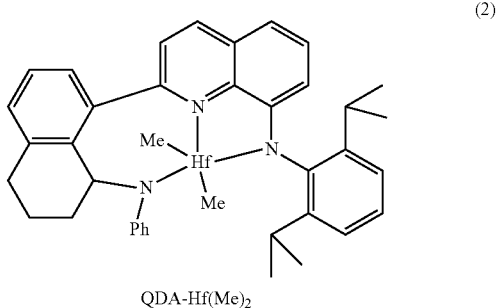

(2)

QDA-Hf(Me)$_2$

Catalysts (transition metal complexes) of the present disclosure can be used in polyolefin polymerizations, for example, as described in U.S. Pat. No. 10,208,140, herein incorporated by reference.

Methods for Making the Ligand Compounds.

The quinolinyldiamine ligands described herein are generally prepared in multiple steps with column chromatography being merely optional at each of the multiple steps. Scheme 1 is an illustrative method for making QDA intermediates, ligands, and catalyst complexes.

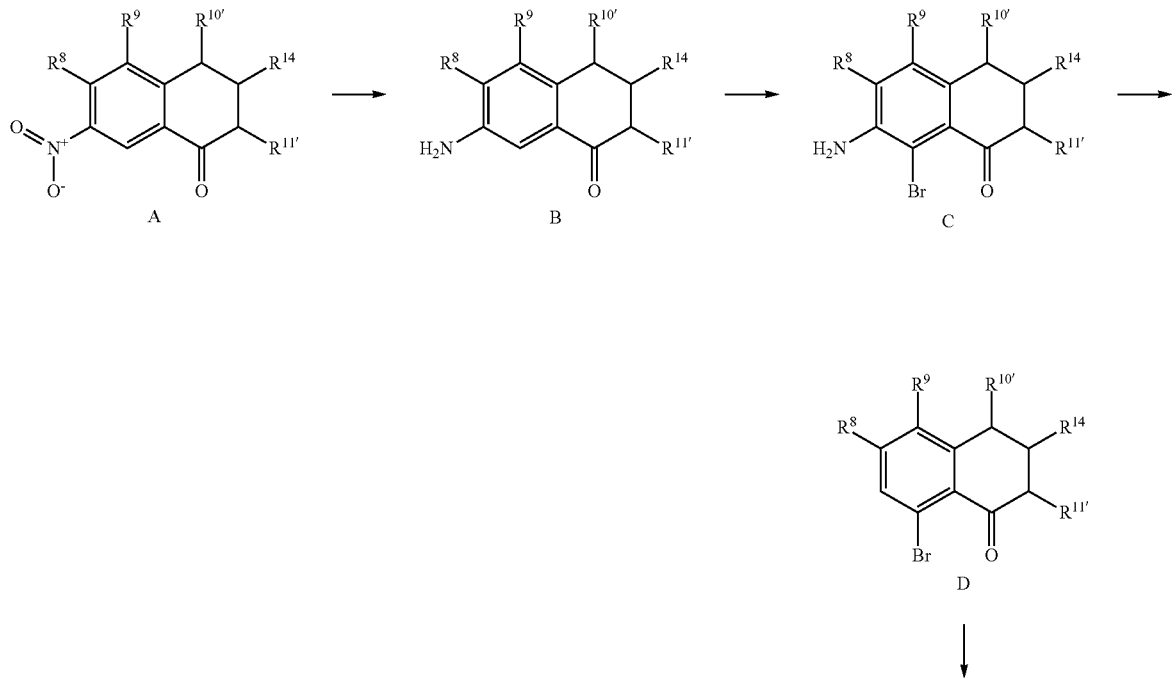

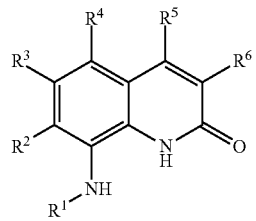

G

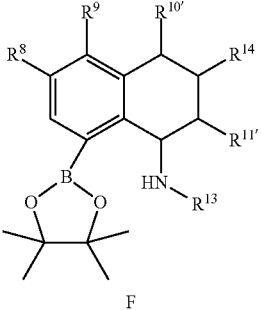

-continued

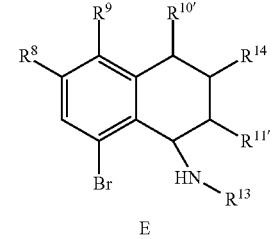

E

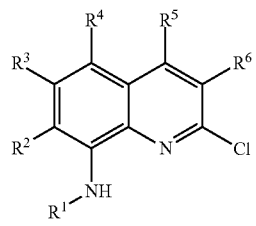

H

+

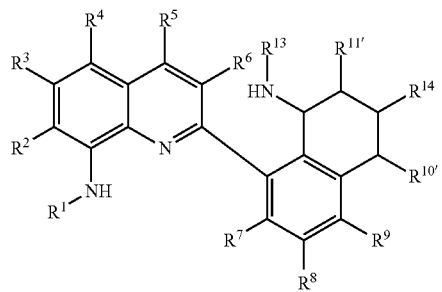

(III)

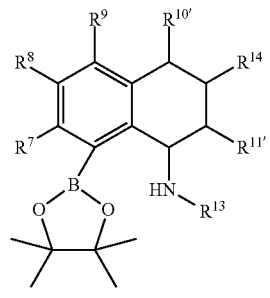

F

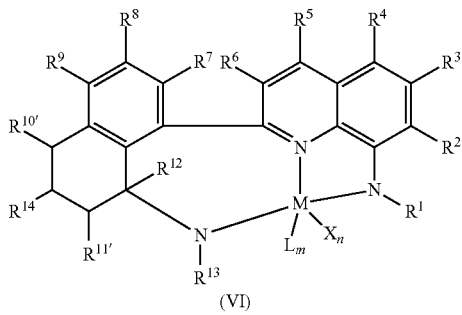

(VI)

M is a Group 3, 4, 5, 6, 7, 8, 9, 10, 11, or 12 metal

The "R" groups of each Formula of Scheme 1 are as described for Formulas (I), (II), (III), (IV), (V) and (VI) above, where applicable. For example, with respect to each Formula of Scheme 1 where applicable, M is a Group 3, 4, 5, 6, 7, 8, 9, 10, 11, or 12 metal (such as a group 4 metal);

X is an anionic leaving group, (such as a hydrocarbyl group or a halogen);

L is a neutral Lewis base;

$R^1$ and $R^{13}$ are independently selected from hydrocarbyl, substituted hydrocarbyl, and silyl groups;

$R^2$, $R^3$, $R^4$, $R^5$, $R^6$, $R^7$, $R^8$, $R^9$, $R^{10'}$, $R^{11'}$, $R^{12}$, and $R^{14}$ are independently hydrogen, hydrocarbyl, alkoxy, silyl, amino, aryloxy, substituted hydrocarbyl, halogen, or phosphino;

n is 1 or 2;

m is 0, 1, or 2, where n+m is not greater than 4; and any two R groups (e.g., $R^1$ & $R^2$, $R^2$ & $R^3$, etc.) may be joined to form a substituted hydrocarbyl, unsubstituted hydrocarbyl, substituted heterocyclic, or unsubstituted heterocyclic, saturated or unsaturated ring, where the ring has 5, 6, 7, or 8 ring atoms and where substitutions on the ring can join to form additional rings;

any two X groups may be joined together to form a dianionic group;

any two L groups may be joined together to form a bidentate Lewis base; and any X group may be joined to an L group to form a monoanionic bidentate group.

A 7-nitro-3,4-dihydronaphthalen-1(2H)-one (Formula A) can be prepared by nitration of 3,4-dihydronaphtalene-1 (2H)-one with a nitrating agent (such as $KNO_3$ or $NaNO_3$) and sulfuric acid to form a reaction mixture. The ratio of moles of nitrating agent to moles of 3,4-dihydronaphtalene-1(2H)-one can be about 1.5, although it can be varied between 1 to 10. The nitration can be performed at any suitable temperature such as from about −80° C. to room temperature, such as from about −20° C. to 0° C. A nitration can be performed using any suitable solvent, such as water, and for any suitable time period, such as from about 30 minutes to about 6 hours. A compound represented by Formula A can be precipitated from the reaction mixture using any suitable solvent, such as an alcohol (e.g., ethanol), can be filtered, and can be dried (e.g., under vacuum and or with heat). The compound represented by Formula A may be recrystallized using any suitable solvent, such as an alcohol (e.g., ethanol).

For embodiments of formulas (I) and (IV) where J is, for example,

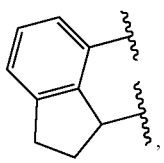

a 6-nitro-2,3-dihydro-1H-inden-1-one (compound represented by Formula P) is substituted for the compound represented by Formula A of Scheme 1. The compound represented by Formula P can be formed using the same or similar process as that used to form the compound represented by Formula A, except that a 2,3-dihydro-1H-inden-1-one is used to form the compound represented by Formula P instead of the 3,4-dihydronaphtalene-1(2H)-one used to form the compound represented by Formula A.

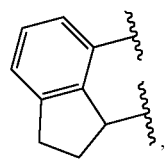 [SMILES: *c1cccc2c1C(*)CC2]

a 6-amino-2,3-dihydro-1H-inden-1-one (compound represented by Formula Q) is substituted for the compound represented by Formula B of Scheme 1. The compound represented by Formula Q can be formed using the same or similar process as that used to form the compound represented by Formula B, except that the compound represented by Formula P is used to form the compound represented by Formula Q instead of the compound represented by Formula A used to form the compound represented by Formula B.

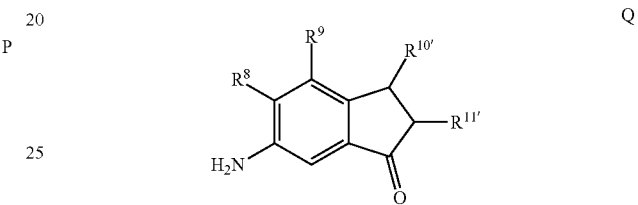

The "R" groups of each Formula of Scheme 1 are as described for Formulas (I), (II), (III), (IV), (V) and (VI) above, where applicable. For example, $R^8$, $R^9$, $R^{10'}$, and $R^{11'}$ are independently hydrogen, hydrocarbyl, alkoxy, silyl, amino, aryloxy, substituted hydrocarbyl, halogen, or phosphino, or any two R groups (e.g., $R^8$ & $R^9$, $R^9$ & $R^{10'}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated or aromatic).

As shown in Scheme 1, the compound represented by Formula A can be reduced to form a 7-amino-3,4-dihydronaphthalen-1(2H)-one (compound represented by Formula B). Reduction can be performed using any suitable reducing agent, such as stannous chloride or stannous bromide. The ratio of moles of reducing agent to moles of 7-nitro-3,4-dihydronaphthalen-1(2H)-one can be about 5, although it can be varied between 1 to 20. A reduction can be performed using any suitable solvent, such as an alcohol (e.g., ethanol), to form a reaction mixture which may be refluxed (e.g., at 78° C.) in the presence of the reducing agent and the compound represented by Formula A to yield the compound represented by Formula B. A reduction can be performed for any suitable time, such as from about 1 hour to about 12 hours, such as about 2 hours. After reflux, an aqueous solution of alkali base (such as NaOH) may be added to the reaction mixture to form a base-containing mixture. The base-containing mixture can be extracted using any suitable organic solvent, such as ether, to form a biphasic mixture, and the organic phase may be (1) dried with a drying agent (e.g., MgSO$_4$ or Na$_2$SO$_4$), (2) filtered, and or (3) evaporated to dryness.

For embodiments of formulas (I) and (IV) where J is, for example,

The "R" groups of each Formula of Scheme 1 are as described for Formulas (I), (II), (III), (IV), (V) and (VI) above, where applicable. For example, $R^8$, $R^9$, $R^{10'}$, and $R^{11'}$ are independently hydrogen, hydrocarbyl, alkoxy, silyl, amino, aryloxy, substituted hydrocarbyl, halogen, or phosphino, or any two R groups (e.g., $R^8$ & $R^9$, $R^9$ & $R^{10'}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated or aromatic).

Scheme 1 further illustrates bromination of the compound represented by Formula B to provide a 7-amino-8-bromo-3,4-dihydronaphthalen-1(2H)-one (compound represented by Formula C). Bromination can be performed by treating the compound represented by Formula B with a brominating agent, such as N-bromosuccinimide (NBS), and in any suitable organic solvent, such as N,N-dimethylformamide, to form a reaction mixture. The ratio of moles of NBS to moles of 7-amino-3,4-dihydronaphthalen-1(2H)-one can be about 0.96, although it can be varied between 0.5 to 5. Bromination may be performed at a temperature of from about −80° C. to about 25° C., such as from about −20° C. to 5° C., such as about 0° C. Bromination may be performed for any suitable time period, such as from about 30 minutes to about 24 hours, such as about 2 hours to about 6 hours, such as about 4 hours. The reaction mixture can be extracted with any suitable organic solvent, such as dichloromethane, which can be further introduced to water to form a biphasic mixture. The organic phase of the biphasic mixture can be dried with a drying agent (e.g., MgSO$_4$ or Na$_2$SO$_4$) and or evaporated to dryness. The dried product can be dissolved in an organic solvent, such as an alcohol (e.g., ethanol) followed by cooling at a temperature such as from about −80° C. to about 10° C., such as about −30° C. to form a precipitated product (7-amino-8-bromo-3,4,-dihydronaphthalen-1(2H)-one (the compound represented by Formula C). The compound represented by Formula C can then be filtered and or dried.

For embodiments of formulas (I) and (IV) where J is, for example,

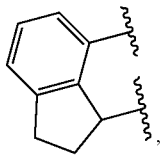 [SMILES: *c1cccc2c1C(*)CC2]

a 6-amino-7-bromo-2,3-dihydro-1H-inden-1-one (compound represented by Formula K) is substituted for the compound represented by Formula C of Scheme 1. The compound represented by Formula K can be formed using the same or similar process as that used to form the compound represented by Formula C, except that the compound represented by Formula H is used to form the compound represented by Formula K instead of the compound represented by Formula B used to form the compound represented by Formula C.

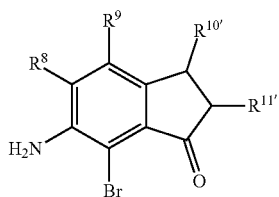

K

The "R" groups of each Formula of Scheme 1 are as described for Formulas (I), (II), (III), (IV), (V) and (VI) above, where applicable. For example, $R^8$, $R^9$, $R^{10'}$, and $R^{11'}$ are independently hydrogen, hydrocarbyl, alkoxy, silyl, amino, aryloxy, substituted hydrocarbyl, halogen, or phosphino, or any two R groups (e.g., $R^8$ & $R^9$, $R^9$ & $R^{10'}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated or aromatic).

Scheme 1 further illustrates deamination of the compound represented by Formula C to provide an 8-bromo-3,4-dihydronaphthalen-1(2H)-one (compound represented by Formula D). Deamination includes treating the compound represented by Formula C with an acid solution (e.g., from about 2 Molar (M) to about 6M, such as about 4M) using any suitable acid, such as HCl. The acid solution can be introduced to the compound represented by Formula C at a temperature of from about −80° C. to room temperature, such as from about 0° C. to about 5° C. To the acid/Formula C mixture, a nitrite can be added (as a solid or as an aqueous solution) to form a nitrite-containing solution. A nitrite can include sodium nitrite, potassium nitrite, or mixtures thereof. The ratio of moles of nitrite to moles of 7-amino-8-bromo-3,4-dihydronaphthalen-1(2H)-one can be of about 1.1, although it can be varied between 0.5 to 5. To the nitrite-containing solution, a phosphorous oxoacid can be added (as a solid or as an aqueous solution). A phosphorous oxoacid can be hypophosphorous acid ($H_3PO_2$). The phosphorous oxoacid can be introduced to the nitrite-containing mixture at a temperature of from about −80° C. to room temperature, such as from about 0° C. to about 10° C. The phosphorous oxoacid containing mixture can be stirred for a time period of from about 1 minute to about 6 hours, such as from about 15 minutes to about 1 hour, after which water may be added to the mixture and extracted with any suitable organic solvent, such as dichloromethane to form a biphasic mixture. The organic phase of the biphasic mixture may be (1) dried with a drying agent (e.g., $MgSO_4$ or $Na_2SO_4$), (2) filtered, and or (3) evaporated to dryness. The recovered compound represented by Formula D can be recrystallized using any suitable organic solvent, such as an alcohol (e.g., ethanol).

For embodiments of Formulas (I) and (IV) where J is, for example,

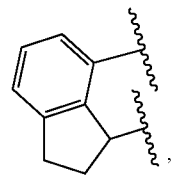

a 7-bromo-2,3-dihydro-1H-inden-1-one (compound represented by Formula L) is substituted for the compound represented by Formula D of Scheme 1. The compound represented by Formula L can be formed using the same or similar process as that used to form the compound represented by Formula D, except that the compound represented by Formula K is used to form the compound represented by Formula L instead of the compound represented by Formula C used to form the compound represented by Formula D.

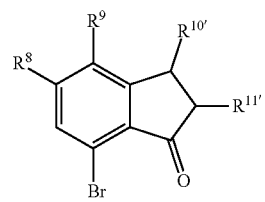

L

The "R" groups of each Formula of Scheme 1 are as described for Formulas (I), (II), (III), (IV), (V) and (VI) above, where applicable. For example, $R^8$, $R^9$, $R^{10'}$, and $R^{11'}$ are independently hydrogen, hydrocarbyl, alkoxy, silyl, amino, aryloxy, substituted hydrocarbyl, halogen, or phosphino, or any two R groups (e.g., $R^8$ & $R^9$, $R^9$ & $R^{10'}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated or aromatic).

Alternatively, the compounds represented by Formulas D and L can be synthesized from a 1,2,3,4-tetrahydronaphthalen-1-ol or a 2,3-dihydro-1H-inden-1-ol, respectively. For example, the 1,2,3,4-tetrahydronaphthalen-1-ol or 2,3-dihydro-1H-inden-1-ol can be introduced to a strong base, such as an alkyl lithium, such as n-butyl lithium in any suitable organic solvent, such as pentane, at a temperature of from about −80° C. to about 25° C., such as about 0° C. If an alkyl lithium base is used, N,N,N',N'-tetramethylethylenediamine (TMEDA) may also be added to the strong base mixture. The strong base mixture can be stirred at a temperature of from about 0° C. to about 100° C., such as about 40° C., for a time period of about 1 hour to about 72 hours, such as about 24 hours. The strong base mixture can then be cooled at a temperature of about −80° C. to about 25° C., such as about 0° C., and a brominating agent can be introduced into the mixture to form a brominating agent mixture. Brominating agents include 1,2-dibromo-1,1,2,2-tetrafluoroethane, 1,2-dibromoethane, bromine, N-bromosuccinimide, bromoform, dibromodimethylsilane, tetrabromosilane, and carbontetrabromide. The brominating agent mixture can be stirred at a temperature of about −80° C. to about 50° C., such as about 25° C. for a time period of about 24 hours to about 120 hours, such as about 72 hours. The brominating agent mixture can then be washed with a chloride solution, such as saturated ammonium chloride, followed by a weak base solution, such as saturated sodium carbonate, to form a biphasic mixture. The organic phase of the biphasic mixture can be dried with a drying agent (e.g., $MgSO_4$), filtered, and concentrated (e.g., to dryness) to provide a bromine-containing product, i.e., an 8-bromo-1,2,3,4-tetrahydronaphthalen-1-ol or a 7-bromo-2,3-dihydro-1H-inden-1-ol. The bromine-containing product is optionally flash chromatographed with silica gel stationary phase and mobile phase of ethyl acetate and hexane. The bromine-containing product can be oxidized using any suitable oxidizing agent in any suitable organic solvent, such as dichloromethane, to form an oxidizing agent mixture. Oxidizing agents include pyridinium chlorochromate, and the like. The oxidizing agent mixture can be stirred for a time period of from about 1 hour to about 72 hours, such as about 6 hours, and or at a temperature of from about −80° C. to about 50° C., such as about 25° C. The oxidizing agent mixture can then be optionally passed through a plug of silica and solvent removed to provide a compound represented by Formula D or Formula L.

Returning to Scheme 1, Scheme 1 further illustrates amination of the compound represented by Formula D to provide an 8-bromo-1,2,3,4-tetrahydronaphthalen-1-yl)amine (compound represented by Formula E). A solution of $TiCl_4$ can be added to an aniline and stirred for a time period of from about 1 minute to about 10 hours, such as from about 10 minutes to about 1 hour. The $TiCl_4$-aniline mixture can be heated at a temperature of from about 30° C. to about 120° C., such as about 90° C. The compound represented by Formula D is added to the mixture. The mixture containing the compound represented by Formula D can be stirred for from about 1 minute to about 10 hours, such as from about 10 minutes to about 1 hour. The mixture containing the compound represented by Formula D can be heated at a temperature of from about 30° C. to about 120° C., such as about 90° C. The mixture containing the compound represented by Formula D can then be introduced to water and extracted with any suitable organic solvent (such as ethyl acetate) to form a biphasic mixture. The organic phase of the biphasic mixture can be dried with a drying agent (e.g., $MgSO_4$ or $Na_2SO_4$) and or evaporated to dryness. The dried product can be dissolved in an organic solvent, such as an alcohol (e.g., ethanol) followed by optional cooling to form a precipitated product. The precipitated product can be dissolved in any suitable organic solvent (such as methanol) and introduced to a reducing agent (such as $NaBH_4$, $NaBH_3CN$, $LiAlH_4$) and a weak acid (such as acetic acid) under an inert atmosphere (such as nitrogen or argon). The mixture containing the precipitated product can be refluxed for a time period of from about 30 minutes to about 10 hours, such as about 3 hours. The mixture can then be cooled (e.g., to room temperature) and evaporated to dryness to form a residue. The residue may be introduced to water and extracted with any suitable organic solvent (such as ethyl acetate) to form a biphasic mixture. The organic phase of the biphasic mixture can be dried with a drying agent (e.g., $MgSO_4$ or $Na_2SO_4$) and or evaporated to dryness to form a dried product. The dried product can be optionally recrystallized by dissolving the dried product in an organic solvent, such as an alcohol (e.g., ethanol) followed by optional cooling to form the precipitated product (8-bromo-1,2,3,4-tetrahydronaphthalen-1-yl)amine (Compound E).

For embodiments of formulas (I) and (IV) where J is, for example,

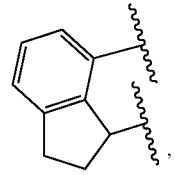 [SMILES: *c1cccc2c1C(*)CC2]

a (7-bromo-2,3-dihydro-1H-inden-1-yl)amine (compound represented by Formula M) is substituted for the compound represented by Formula E of Scheme 1. The compound represented by Formula M can be formed using the same or similar process as that used to form the compound represented by Formula E, except that the compound represented by Formula L is used to form the compound represented by Formula M instead of the compound represented by Formula D used to form the compound represented by Formula E.

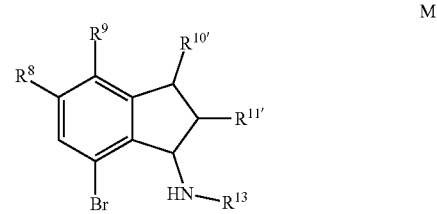

The "R" groups of each Formula of Scheme 1 are as described for Formulas (I), (II), (III), (IV), (V) and (VI) above, where applicable. For example, $R^{13}$ is selected from hydrocarbyl, substituted hydrocarbyl, and silyl groups; $R^8$, $R^9$, $R^{10'}$, and $R^{11'}$ are independently hydrogen, hydrocarbyl, alkoxy, silyl, amino, aryloxy, substituted hydrocarbyl, halogen, or phosphino, or any two R groups (e.g., $R^8$ & $R^9$, $R^9$ & $R^{10'}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated or aromatic).

Scheme 1 further illustrates borylation of the compound represented by Formula E to form an 8-(4,4,5,5-tetramethyl-1,3,2-dioxaborolan-2-yl)-1,2,3,4-tetrahydronaphthalen-1-amine (compound represented by Formula F). A solution of the compound represented by Formula E in any suitable organic solvent (such as tetrahydrofuran) can be treated with a lithiating agent (such as tert-butyl lithium in pentane) and stirred for from about 1 minute to about 10 hours, such as about 1 hour. The mixture of the compound represented by Formula E and lithiating agent can be from about −100° C. to about 0° C., such as from about −80° C. to about 0° C., such as at −80° C. Alternatively, the mixture of the compound represented by Formula E and lithiating agent can be at 0° C. A borolane is then added to the mixture to form a borolane mixture. Borolanes include 2-isopropoxy-4,4,5,5-tetramethyl-1,3,2-dioxaborolane, triisopropylborate, and triethylborate. The borolane mixture can be stirred for from about 1 minute to about 10 hours, such as about 1 hour and or at a temperature of from about −80° C. to about 40° C., such as about 20° C. The borolane mixture can then be quenched with water and optionally evaporated to dryness to form a residue. The residue can be diluted with water and extracted with any suitable organic solvent (such as ethyl acetate) to form a biphasic mixture. The organic phase of the biphasic mixture can be dried with a drying agent (e.g., $MgSO_4$ or $Na_2SO_4$) and or evaporated to dryness to form a dried product. The dried product can be optionally recrystallized by dissolving the dried product in an organic solvent, such as an alcohol (e.g., ethanol) followed by optional cooling to form the precipitated product 8-(4,4,5,5-tetramethyl-1,3,2-dioxaborolan-2-yl)-1,2,3,4-tetrahydronaphthalen-1-amine (the compound represented by Formula F).

For embodiments of formulas (I) and (IV) where J is, for example,

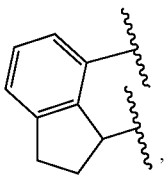

a 7-(4,4,5,5-tetramethyl-1,3,2-dioxaborolan-2-yl)-2,3-dihydro-1H-inden-1-amine (compound represented by Formula N) is substituted for the compound represented by Formula F of Scheme 1. The compound represented by Formula N can be formed using the same or similar process as that used to form the compound represented by Formula F, except that the compound represented by Formula M is used to form the compound represented by Formula N instead of the compound represented by Formula E used to form the compound represented by Formula F.

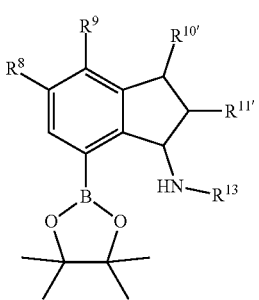

N

The "R" groups of each Formula of Scheme 1 are as described for Formulas (I), (II), (III), (IV), (V) and (VI) above, where applicable. For example, $R^{13}$ is selected from hydrocarbyl, substituted hydrocarbyl, and silyl groups; $R^8$, $R^9$, $R^{10'}$, and $R^{11'}$ are independently hydrogen, hydrocarbyl, alkoxy, silyl, amino, aryloxy, substituted hydrocarbyl, halogen, or phosphino, or any two R groups (e.g., $R^8$ & $R^9$, $R^9$ & $R^{10'}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated or aromatic).

As shown in Scheme 1, an 8-(amino)quinolin-2(1H)-one (compound represented by Formula G) is used. The compound represented by Formula G can be obtained by treating an 8-bromoquinolin-2(1H)-one with a strong base (such as triethyl amine or sodium hydride (NaH) in tetrahydrofuran solvent) to form a strong base mixture. The strong base can be added to a solution of the 8-bromoquinolin-2(1H)-one at a temperature of from about −80° C. to about 30° C., such as about 0° C. to about 25° C. The strong base mixture can be stirred at a temperature of from about −80° C. to about 60° C., such as about 25° C., for a period of time such as from about 1 minute to about 10 hours, such as about 30 minutes. The ratio of moles of base to moles of 8-bromoquinolin-2(1H)-one can be about 1.0, although ratios between 0.8 to 5 may be used. The strong base mixture can then be brought to a temperature of from about −20° C. to about 25° C., such as about 0° C., followed by the addition of silylating agent to form a silylating agent mixture. Silylating agents include tert-butyl-dimethylsilylchloride (TB-DMSCl), chlorotrimethylsilane, chlorotriethylsilane, and tert-butyldimethylsilylbromide. The ratio of moles of silylating agent to moles of 8-bromoquinolin-2(1H)-one can be about 1.0, although ratios between 0.8 to 10 may be used. The silylating agent mixture can be stirred for from about 1 minute to about 5 hours, such as about 30 minutes. The silylating agent mixture can be contacted with water and any suitable organic solvent (such as ethyl acetate) to form a biphasic mixture. The organic phase of the biphasic mixture can be dried with a drying agent (e.g., $MgSO_4$ or $Na_2SO_4$) and or evaporated to dryness to form a dried product. A solution of an aniline in any suitable organic solvent (such as toluene) can be treated with a lithiating agent (such as n-BuLi) and optionally heated at a temperature of from about 30° C. to about 130° C., such as about 100° C., followed by allowing the solution to cool. To this mixture a palladium agent and phosphorous ligand are added to form a palladium mixture. A palladium agent can be $Pd_2(dibenzylideneacetone)_3$, palladium acetate, tetrakis(triphenylphosphine)palladium, or palladium dichloride. The ratio of moles of palladium to moles of 8-bromoquinolin-2(1H)-one can be about 0.02, although ratios between 0.005 to 0.2 may be used. A phosphorous ligand can be triphenyl phosphine, 2-dicyclohexylphosphino-2',4',6'-triisopropylbiphenyl (XPhos). The ratio of moles of phosphine to moles of palladium can be about 2, although ratios between 0.8 to 5 may be used. The dried protected silylated 8-bromoquinolin-2(1H)-one can be added to the palladium mixture and heated at a temperature of from about 30° C. to about 100° C., such as about 60° C. The mixture can then be cooled, and water can then be added to the mixture followed by any suitable organic solvent (such as ethyl acetate) to form a biphasic mixture. The organic phase of the biphasic mixture can be dried with a drying agent (e.g., $MgSO_4$ or $Na_2SO_4$) and or evaporated to dryness to form a dried product. The dried product can be dissolved in any suitable organic solvent (such as dichloromethane, methanol, or mixtures thereof), and an acid (such as HCl (3M to 15M, such as 12M) can be added to this solution to form an acid mixture. The acid mixture can be stirred for from about 1 hour to about 6 hours, such as about 3 hours, and then introduced to a neutralizing solution (such as $K_2CO_3$, such as 5% $K_2CO_3$) and evaporated to dryness to form a dried product containing 8-(amino)quinolin-2(1H)-one (the compound represented by Formula G). The dried product can be recrystallized using any suitable organic solvent, such as hexanes.

Alternatively, the compound represented by Formula G can be formed by treating a cinnamic acid with oxalyl chloride to form a cinnamoyl chloride in any suitable organic solvent, such as dimethylformamide, dichloromethane, or a mixture thereof. The oxalyl chloride can be introduced to a mixture of the cinnamic acid in solvent, to form a reaction mixture, at a temperature of from about −80° C. to about 25° C., such as about 0° C., and the reaction mixture can be stirred for a time period of about 30 minutes to about 24 hours, such as about 4 hours. The solvent of the reaction mixture can then be evaporated (e.g., to dryness) to provide a cinnamoyl chloride product. The cinnamoyl chloride product can be introduced to a 2-bromoaniline, to form an aniline mixture, in any suitable solvent, such as water, acetone, or a mixture thereof. The aniline mixture can be stirred for a time period of about 10 minutes to about 12 hours, such as about 2 hours, and or at a temperature of from about −10° C. to about 25° C., such as about 0° C. The solvent can be partially or fully removed (e.g., evaporated) from the aniline mixture and an N-(2-bromophenyl)cinnamide can be obtained (e.g., by filtration). The N-(2-bromophenyl)cinnamide may then be treated with aluminum chloride ($AlCl_3$) in any suitable solvent, such as chlorobenzene, to form a reaction mixture. The reaction mixture can be stirred for a period of time such as about 10 minutes to about 24 hours, such as about 30 minutes, and or at a temperature of from about 50° C. to about 200° C., such as about 120° C. The reaction mixture can then be cooled to a suitable temperature (e.g., from about 25° C. to about 50° C.) and introduced to water to form a precipitate of the compound represented by Formula G that can be isolated by filtration.

Returning to Scheme 1, Scheme 1 illustrates that the compound represented by Formula G is chlorinated to form a 2-chloro-N-(phenyl)quinolin-8-amine (compound represented by Formula H). The compound represented by Formula G can be treated, neat or in the presence of an organic solvent, with a chlorinating agent to form a chlorinating agent mixture. Chlorinating agents include phosphorous oxychloride, phosphorous trichloride, phosphorous pentachloride, thionylchloride, tetrachlorosilane, trichloroethylsilane, and dichlorodimethylsilane. The ratio of moles of chlorinating agent to moles of 8-(amino)quinolin-2(1H)-one can be about 47, although ratios between 1 to 100 may be used. The chlorinating agent mixture can be heated at a temperature of from about 30° C. to about 140° C., such as about 100° C., and/or for a period of time from about 1 hour to about 72 hours, such as about 48 hours. The chlorinating agent mixture can be introduced to water (such as ice) and any suitable organic solvent (such as diethyl ether) to form a biphasic mixture. The organic phase of the biphasic mixture can be dried with a drying agent (e.g., $K_2CO_3$) and or then evaporated to dryness to form a dried product containing 2-chloro-N-(phenyl)quinolin-8-amine (the compound represented by Formula H). The dried product can be recrystallized using any suitable organic solvent, such as hexanes.

Scheme 1 further illustrates a ligand represented by Formula (III) formed by coupling the compound represented by Formula H with the compound represented by Formula F. To a solution of the 2-chloro-N-(phenyl)quinolin-8-amine (the compound represented by Formula H), in any suitable organic solvent (such as dioxane), is added 8-(4,4,5,5-tetramethyl-1,3,2-dioxaborolan-2-yl)-1,2,3,4-tetrahydronaphthalen-1-amine (the compound represented by Formula F), a weak base (such as cesium carbonate) and a palladium agent to form a mixture. Palladium agents include $Pd(Ph_3)_4$, palladium acetate, palladium di(benzylideneacetone), and palladium dichloride. The ratio of moles of palladium agent to moles of 2-chloro-N-(phenyl)quinolin-8-amine can be about 0.05, although ratios between 0.005 to 0.2 may be used. The mixture may be stirred for a period of time from 5 minutes to about 10 hours, such as about 2 hours, and or at a temperature of from about 30° C. to about 150° C., such as about 90° C. After cooling to ambient temperature, a non-polar solvent can be added to the mixture and extracted with water to form a biphasic mixture. The organic phase of the biphasic mixture can be further extracted with brine and or water. The organic phase of the biphasic mixture can be filtered (to remove traces of phosphine oxide (if any) and dried with a drying agent (e.g., $MgSO_4$ or $Na_2SO_4$) and or evaporated to dryness to form a dried product containing a ligand represented by Formula (III). The dried product can be recrystallized using any suitable organic solvent, such as hexanes.

For embodiments of formulas (I) and (IV) where J is, for example,

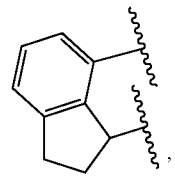

a 7-(4,4,5,5-tetramethyl-1,3,2-dioxaborolan-2-yl)-2,3-dihydro-1H-inden-1-amine (compound represented by Formula N), as described above, is substituted for the compound represented by Formula F of Scheme 1. Ligands represented by Formula (I) can be formed using the same or similar process as that used to form ligands represented by Formula (III) except that the compound represented by Formula H is coupled with the compound represented by Formula N to form a ligand represented by Formula (I), instead of coupling the compound represented by Formula H with the compound represented by Formula F to form a ligand represented by Formula (III).

Methods for Making the Metal Complexes

In another aspect of the present disclosure there are provided various processes for synthesizing the complexes described herein. In at least one embodiment, a metal complex is represented by Formula (IV), (V), or (VI), as described above.

One method for making transition metal quinolinyldiamido complexes is by reaction of the quinolinyldiamine ligand with a metal reactant containing anionic basic leaving groups. Suitable anionic basic leaving groups include dialkylamido, benzyl, phenyl, hydrido, and methyl. In this reaction, the role of the basic leaving group is to deprotonate the quinolinyldiamine ligand. Suitable metal reactants for this type of reaction include, but are not limited to, $HfBn_4$ ($Bn=CH_2Ph$), $ZrBn_4$, $TiBn_4$, $ZrBn_2Cl_2(OEt_2)$, $HfBn_2Cl_2(OEt_2)_2$, $Zr(NMe_2)_2C_{12}$(dimethoxyethane), $Hf(NMe_2)_2C_{12}$(dimethoxyethane), $Hf(NMe_2)_4$, $Zr(NMe_2)_4$, and $Hf(NEt_2)_4$. In one example, $Hf(NMe_2)_4$ is reacted with a quinolinyldiamine ligand at elevated temperatures to form the quinolinyldiamido complex with the formation of two molar equivalents of dimethylamine, which is lost or removed before the quinolinyldiamido complex is isolated. Any suitable organic solvent may be used, such as toluene. The reaction mixture can be heated at a temperature of from about 30° C. to about 130° C., such as about 85° C.

A second method for making transition metal quinolinyldiamido complexes is by reaction of the quinolinyldiamine ligand with an alkali metal or alkaline earth metal base (e.g., BuLi, EtMgBr) to deprotonate the ligand, followed by reaction with a metal halide (e.g., HfCl$_4$, ZrCl$_4$).

With either method of forming a transition metal quinolinyldiamido complex, the reaction mixtures may be cooled and filtered to provide the isolated complex.

This invention further relates to:
1. A method for making a quinolinyldiamine, comprising:
   introducing an acid solution, a nitrite, and phosphorous oxoacid to a compound represented by Formula C or Formula K:

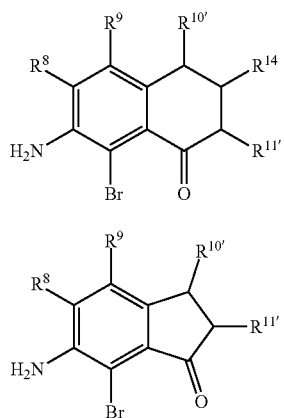

C

K wherein R$^8$, R$^9$, R$^{10'}$, R$^{11'}$, and R$^{14}$ are independently hydrogen, hydrocarbyl, alkoxy, silyl, amino, aryloxy, substituted hydrocarbyl, halogen, or phosphino, or any two of R$^8$ & R$^9$, R$^9$ & R$^{10'}$, R$^{10'}$ & R$^{14}$, and R$^{10'}$ & R$^{11'}$ are joined to form a substituted or unsubstituted hydrocarbyl or heterocyclic ring, wherein the ring has 5, 6, 7, or 8 ring atoms, and wherein the ring is saturated or unsaturated; and obtaining a compound represented by Formula D or Formula L:

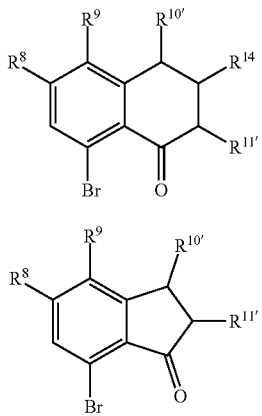

D

L wherein R$^8$, R$^9$, R$^{10'}$, R$^{11'}$, and R$^{14}$ are independently hydrogen, hydrocarbyl, alkoxy, silyl, amino, aryloxy, substituted hydrocarbyl, halogen, or phosphino, or any two of R$^8$ & R$^9$, R$^9$ & R$^{10'}$, R$^{10'}$ & R$^{14}$, and R$^{10'}$ & R$^{11'}$ are joined to form a substituted or unsubstituted hydrocarbyl or heterocyclic ring, wherein the ring has 5, 6, 7, or 8 ring atoms, and wherein the ring is saturated or unsaturated.

2. The method of paragraph 1, wherein introducing comprises:
   mixing the acid solution with the compound represented by Formula C or Formula K to form a first mixture;
   mixing the nitrite with the first mixture to form a second mixture; and
   mixing the phosphorous oxoacid with the second mixture to form a third mixture.
3. The method of paragraphs 1 or 2, further comprising contacting the compound represented by Formula D or Formula L with an organic solvent.
4. The method of paragraph 3, wherein the organic solvent is an alcohol.
5. The method of paragraphs 1 to 4, wherein the acid solution is a 2M to 6M solution of HCl.
6. The method of any of paragraphs 1 to 5, wherein the nitrite is sodium nitrite, potassium nitrite, or mixtures thereof.
7. The method of any of paragraphs 1 to 6, wherein the phosphorous oxoacid is hypophosphorous acid.
8. The method of any of paragraphs 1 to 7, further comprising:
   introducing TiCl$_4$ and an aniline to the compound represented by Formula D or Formula L.
9. The method of paragraph 8, wherein introducing comprises:
   mixing the TiCl$_4$ with the aniline to form a fourth mixture;
   heating the fourth mixture at a temperature of from about 30° C. to about 120° C.;
   mixing the compound represented by Formula D or Formula L to form a fifth mixture;
   heating the fifth mixture at a temperature of from about 30° C. to about 120° C.; and
   obtaining a dried product from the fifth mixture.
10. The method of paragraph 9, further comprising introducing the dried product to a reducing agent and an acid.
11. The method of paragraph 10, wherein:
    the reducing agent is selected from NaBH$_4$, NaBH$_3$CN, and LiAlH$_4$, and
    the acid is acetic acid.
12. The method of any of paragraphs 8 to 11, further comprising:
    obtaining a compound represented by Formula E or Formula M:

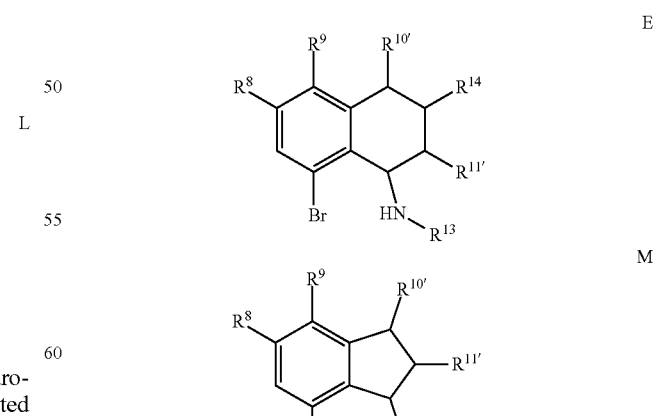

E

M wherein R$^{13}$ is selected from hydrocarbyl, substituted hydrocarbyl, and silyl group, and $R^8$, $R^9$, $R^{10'}$, $R^{11'}$, and $R^{14}$ are independently hydrogen, hydrocarbyl, alkoxy, silyl, amino, aryloxy, substituted hydrocarbyl, halogen, or phosphino, or any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated.

13. The method of paragraph 12, further comprising contacting the compound represented by Formula E or Formula M with an organic solvent.

14. The method of paragraph 13, wherein the organic solvent is an alcohol.

15. The method of any of paragraphs 8 to 14, further comprising:
introducing a lithiating agent and a borolane to the compound represented by Formula E or Formula M; and
obtaining a compound represented by Formula F or Formula N:

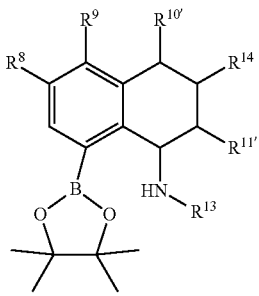

F

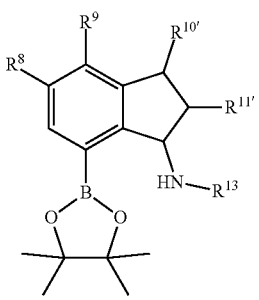

N wherein $R^{13}$ is selected from hydrocarbyl, substituted hydrocarbyl, and silyl group, and
$R^8$, $R^9$, $R^{10'}$, and $R^{11'}$ are independently hydrogen, hydrocarbyl, alkoxy, silyl, amino, aryloxy, substituted hydrocarbyl, halogen, or phosphino, or any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated.

16. The method of paragraph 15, wherein introducing comprises:
mixing the lithiating agent and the compound represented by Formula E or Formula M to form a sixth mixture;
mixing the borolane with the sixth mixture to form a seventh mixture, and the sixth mixture is at a temperature of from about −100° C. to about 0° C.

17. The method of paragraph 16, wherein the borolane is 2-isopropoxy-4,4,5,5-tetramethyl-1,3,2-dioxaborolane.

18. The method of any paragraphs 15 to 17, further comprising contacting the compound represented by Formula F or Formula N with an organic solvent.

19. The method of paragraph 18, wherein the organic solvent is an alcohol.

20. The method of any of paragraphs 15 to 19, further comprising introducing a base, a palladium agent, and the compound represented by Formula F or Formula N to a compound represented by Formula H:

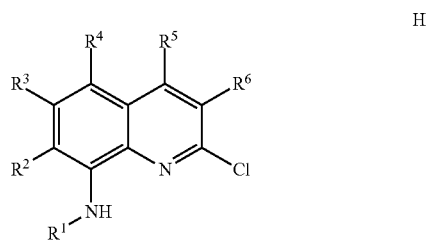

H wherein $R^1$ is selected from hydrocarbyl, substituted hydrocarbyl, and silyl group, and
$R^2$, $R^3$, $R^4$, $R^5$, and $R^6$ are independently hydrogen, hydrocarbyl, alkoxy, silyl, amino, aryloxy, substituted hydrocarbyl, halogen, or phosphino, or any two of $R^2$ & $R^3$, $R^3$ & $R^4$, and $R^5$ & $R^6$ are joined to form a substituted or unsubstituted hydrocarbyl or heterocyclic ring, wherein the ring has 5, 6, 7, or 8 ring atoms, and wherein the ring is saturated or unsaturated; and
obtaining a quinolinyldiamine.

21. The method of paragraph 20, wherein the quinolinyldiamine is represented by Formula (I):

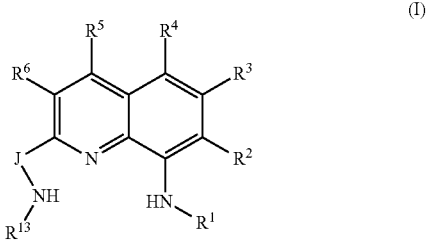

(I)

wherein:
$R^1$ and $R^{13}$ are independently selected from hydrocarbyl, substituted hydrocarbyl, and silyl group;
$R^2$, $R^3$, $R^4$, $R^5$, and $R^6$ are independently selected from hydrogen, hydrocarbyl, alkoxy, silyl, amino, aryloxy, substituted hydrocarbyl, halogen, and phosphino;
any two adjacent R groups may be joined to form a substituted or unsubstituted hydrocarbyl or heterocyclic ring, wherein the ring has 5, 6, 7, or 8 ring atoms and wherein substitutions on the ring can join to form additional rings;
J is

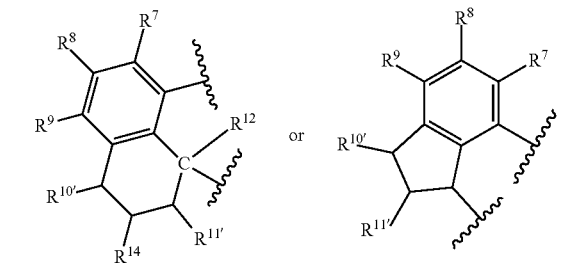

wherein $R^7$, $R^8$, $R^9$, $R^{10'}$, $R^{11'}$, and $R^{14}$ are independently hydrogen, hydrocarbyl, alkoxy, silyl, amino, aryloxy, substituted hydrocarbyl, halogen, or phosphino, or any two R groups may be joined to form a substituted or unsubstituted hydrocarbyl or heterocyclic ring, where the ring has 5, 6, 7, or 8 ring atoms, said ring may be saturated or unsaturated, and wherein ⁒ indicates connection to the ligand.

22. The method of paragraphs 20 or 21, wherein the base is cesium carbonate and the palladium agent is Pd(Ph$_3$)$_4$.

23. The method of any of paragraphs 20 to 22, further comprising contacting the quinolinyldiamine with an organic solvent.

24. The method of paragraph 23, wherein the organic solvent is hexane.

25. The method of any of paragraphs 20 to 24, further comprising:
introducing the quinolinyldiamine to a transition metal; and
obtaining a transition metal quinolinyldiamido complex.

26. The method of paragraph 25, wherein the metal quinolinyldiamido complex is:

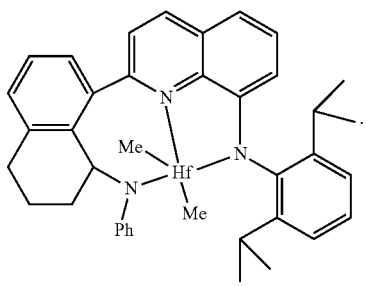

(2)

27. The method of any of paragraphs 1 to 26, further comprising:
obtaining the compound represented by Formula C or Formula K by introducing a brominating agent to a compound represented by Formula B or Formula Q:

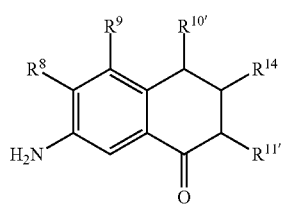

B

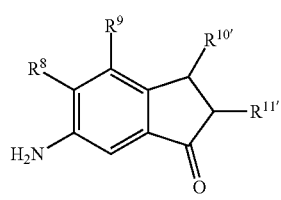

Q wherein $R^8$, $R^9$, $R^{10'}$, $R^{11'}$, and $R^{14}$ are independently hydrogen, hydrocarbyl, alkoxy, silyl, amino, aryloxy, substituted hydrocarbyl, halogen, or phosphino, or any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated.

28. The method of paragraph 27, wherein the brominating agent is N-bromosuccinimide.

29. The method of any of paragraphs 1 to 28, further comprising:
obtaining the compound represented by Formula B or Formula Q by introducing a reducing agent to a compound represented by Formula A or Formula P:

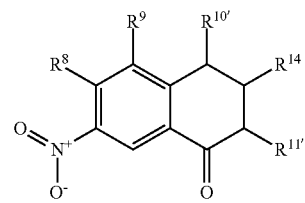

A

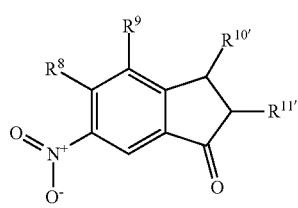

P wherein $R^8$, $R^9$, $R^{10'}$, $R^{11'}$, and $R^{14}$ are independently hydrogen, hydrocarbyl, alkoxy, silyl, amino, aryloxy, substituted hydrocarbyl, halogen, or phosphino, or any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated.

30. The method of paragraph 29, wherein the reducing agent is stannous chloride or stannous bromide.

31. The method of paragraphs 29 or 30, further comprising contacting the compound represented by Formula B or Formula Q with an organic solvent.

32. The method of paragraph 31, wherein the organic solvent is an alcohol.

33. The method of any of paragraphs 1 to 32, further comprising:
obtaining the compound represented by Formula A or Formula P by introducing a 3,4-dihydronaphtalene-1(2H)-one or a 2,3-dihydro-1H-inden-1-one to a nitrating agent and an acid.

34. The method of paragraph 33, wherein the nitrating agent is KNO$_3$ or NaNO$_3$ and the acid is sulfuric acid.

35. The method of paragraphs 33 or 34, further comprising contacting the compound represented by Formula A or Formula P with an organic solvent.

36. The method of paragraph 35, wherein the organic solvent is an alcohol.

EXAMPLES

All air sensitive procedures were performed under a purified argon or nitrogen atmosphere using standard glove box and/or Schlenk line techniques. All solvents used were anhydrous, de-oxygenated and purified according to known techniques. 2-Isopropoxy-4,4,5,5-tetramethyl-1,3,2-dioxaborolane (Aldrich), aniline (Acros), 2,6-diisopropylaniline (Acros), 2.5 M n-BuLi in hexanes (Chemetall GmbH), 1.9 M t-BuLi in pentane (Chemetall GmbH), NaBH$_3$CN (Aldrich), tetrahydronaphtalen-1-one (Merck), Pd(PPh$_3$)$_4$ (Aldrich), TiCl$_4$ (Merck), triethylamine (Acros), THF (Merck), diethyl ether (Merck), ethyl acetate (Merck), methanol (Merck), toluene (Merck), hexanes (Merck), dichloromethane (Merck), acetonitrile (Merck), TsOH (Aldrich), DMF (Aldrich), NBS (Merck), Na$_2$CO$_3$×10H$_2$O (Merck), Na$_2$SO$_4$ (Akzo Nobel), silica gel 60 (40-63 m; Merck), glacial acetic acid (Merck) and CDCl$_3$ (Deutero GmbH) were used as received. Diethyl ether and THF for organometallic synthesis were freshly distilled from sodium benzophenone ketyl. 8-Bromoquinolin-2(1H)-one was prepared from 2-bromoaniline (Acros) and cinnamic acid (Aldrich) as described in [*European Journal of Organic Chemistry*, 2003, v. 8, pp. 1559-1568].

The synthesis of each intermediate involved in the improved synthesis of 2-(8-anilino-5,6,7,8-tetrahydronaphthalen-1-yl)-N-(2,6-diisopropylphenyl)quinolin-8-amine are listed below.

Example 1

Intermediate
7-nitro-3,4-dihydronaphthalen-1(2H)-one

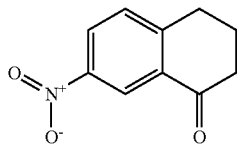 [SMILES: O=C1CCCc2ccc([N+](=O)[O-])cc21]

3,4-Dihydronaphthalen-1(2H)-one (132 g, 900 mmol) was added dropwise to 98% sulfuric acid (900 mL) over 30 min at −10° C. Then, a solution of KNO$_3$ (137 g, 1.35 mol) in 98% sulfuric acid (450 mL) was added dropwise over 2 hours at −10° C. The resulting mixture was stirred for 30 minutes at this temperature. The reaction mixture was then poured into a mixture of crushed ice (4 kg) and water (4 L). The resulting yellowish precipitate was isolated by filtration and washed with water (5×800 mL) and EtOH (400 mL). The precipitate was air-dried overnight to give 146 g of a ca. 4:1 mixture of 7-nitro-3,4-dihydronaphthalen-1(2H)-one and 5-nitro-3,4-dihydronaphthalen-1(2H)-one. The residue was re-crystallized from i-PrOH (900 mL) to afford pure 7-nitro-3,4-dihydronaphthalen-1(2H)-one. Yield 73.0 g (42%) of a dark brown crystalline solid. $^1$H NMR (CDCl$_3$): δ 8.82 (s, 1H, 8-H); 8.27 (d, J=8.4 Hz, 1H, 6-H); 7.44 (d, J=8.2 Hz, 1H, 5-H), 3.07 (t, J=5.8 Hz, 2H, 4,4'-H); 2.72 (t, J=6.1 Hz, 2H, 2,2'-H); 2.08 (m, 2H, 3,3'-H).

Example 2

Intermediate
7-amino-3,4-dihydronaphthalen-1(2H)-one

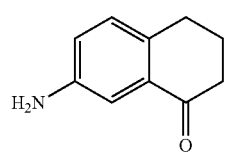

SnCl$_2$.H$_2$O (430 g, 1.91 mol) was added in one portion to a solution of 7-nitro-3,4-dihydronaphthalen-1(2H)-one (73.0 g, 380 mmol) in 95% EtOH (1700 mL). The resulting mixture was heated to reflux for 2 hours. Then, a solution NaOH (180 g) in water (1800 mL) was added portionwise to give a yellow suspension (pH=8-9). This suspension was divided into two parts, and each of them was extracted with diethyl ether (3×300 mL). The combined organic extracts were evaporated to dryness, and the residue was dissolved in diethyl ether (1,000 mL). The resulting dark solution was washed with water, dried over Na$_2$SO$_4$, and passed through a silica gel pad (250 mL). The obtained elute was evaporated to dryness to give 45.1 g (74%) of a dark red crystalline solid. $^1$H NMR (DMSO-d$_6$): δ 7.08 (s, 1H, 8-H); 7.00 (d, J=8.0 Hz, 1H, 5-H); 6.78 (d, J=8.1 Hz, 1H, 6-H), 5.15 (s, 2H, —NH$_2$), 2.75 (m, 2H, 4,4'-H); 2.51 (m, 2H, 2,2'-H); 1.96 (m, 2H, 3,3'-H).

Example 3

Intermediate
7-amino-8-bromo-3,4-dihydronaphthalen-1(2H)-one

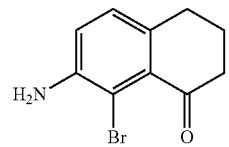 [SMILES: Nc1ccc2c(c1Br)C(=O)CCC2]

A solution of N-bromosuccinimide (47.3 g, 270 mmol) in N,N-dimethylformamide (300 mL) was added dropwise over 3 hours to a solution of 7-amino-3,4-dihydronaphthalen-1(2H)-one (45.1 g, 280 mmol) N,N-dimethylformamide (500 mL) that was cooled to 0° C. The resulting mixture was stirred for 1 hour and then poured into water (1,000 mL). The crude product was extracted with dichloromethane (3×300 mL), and the combined extracts were washed with water (3×500 mL). Further on, the organic phase was dried over Na$_2$SO$_4$, passed through a silica gel pad (100 mL), and the elute was evaporated to dryness to give a ca. 11:1 mixture of 7-amino-8-bromo-3,4-dihydronaphthalen-1(2H)-one and 7-amino-6-bromo-3,4-dihydronaphthalen-1(2H)-one as a dark viscous oil. This mixture was dissolved in 230 mL of 95% EtOH. Crystalline product precipitated from this solution at −30° C. was collected and dried in vacuum. Yield 46.4 g (69%) of a dark red crystalline solid. $^1$H NMR (CDCl$_3$): 6.98 (d, J=8.2 Hz, 1H, 5-H); 6.86 (d, J=8.2 Hz, 1H, 6-H), 4.30 (br. s, 2H, —NH$_2$), 2.84 (m, 2H, 4,4'-H); 2.64 (m, 2H, 2,2'-H); 2.04 (m, 2H, 3,3'-H).

Example 4

Intermediate
8-bromo-3,4-dihydronaphthalen-1(2H)-one

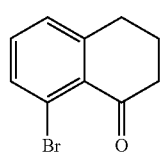 [SMILES: O=C1CCCc2cccc(Br)c21]

At 3° C., 7-amino-8-bromo-3,4-dihydronaphthalen-1 (2H)-one (46.4 g, 193 mmol) was added in one portion to 4M HCl (600 mL). Then, a solution of NaNO₂ (14.7 g, 212 mmol) in water (100 mL) was added dropwise over 1 hour at this temperature. Then, an aqueous solution of 50% H₃PO₂ (200 mL) was added dropwise over 30 min at 5° C. The resulting mixture was diluted with water (500 mL), and the crude product was extracted with dichloromethane (3×300 mL). The combined extracts were dried over Na₂SO₄, passed through a silica gel pad (100 mL), and evaporated to dryness. The residue was washed with small portion of n-hexane and then dried in vacuum. Yield 33.9 g (78%) of a dark red crystalline solid. ¹H NMR (CDCl₃): δ 7.53 (m, 1H, 7-H); 7.18-7.22 (m, 2H, 5,6-H); 2.95 (t, J=6.1 Hz, 2H, 4,4'-H); 2.67 (t, J=6.6 Hz, 2H, 2,2'-H); 2.08 (quint, J=6.1 Hz, J=6.6 Hz, 2H, 3,3'-H).

Example 5

Intermediate (8-bromo-1,2,3,4-tetrahydronaphthalen-1-yl)phenylamine

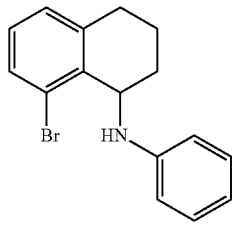 [SMILES: Brc1cccc2c1C(Nc1ccccc1)CCC2]

A solution of TiCl₄ (28.5 g, 150 mmol) in toluene (150 mL) was added dropwise over 30 minutes to a stirred solution of aniline (57.7 g, 620 mmol) in toluene (1500 mL) under argon atmosphere. The resulting mixture was stirred for 30 minutes at 90° C. followed by addition of 8-bromo-3,4-dihydronaphthalen-1(2H)-one (13.1 g, 150 mmol). This mixture was stirred for 30 minutes at 90° C., then cooled to room temperature, and poured into water (500 mL). The product was extracted with ethyl acetate (3×50 mL). The combined organic extracts were dried over Na₂SO₄, evaporated to dryness, and the residue was re-crystallized from f ethyl acetate (30 mL). The obtained crystalline solid was dissolved in methanol (200 mL). To this solution were added NaBH₃CN (9.24 g, 147 mmol) and acetic acid (3 mL) under an argon atmosphere. This mixture was heated to reflux for 3 hours. The mixture was then cooled to room temperature and evaporated to dryness. The residue was diluted with water (200 mL), and the crude product was extracted with ethyl acetate (3×100 mL). The combined organic extracts were dried over Na₂SO₄, and evaporated to dryness. Yield 30.0 g (65%) of a yellow oil. ¹H NMR (CDCl₃): δ 7.44 (m, 1H), 7.21 (m, 2H), 7.05-7.11 (m, 2H), 6.68-6.73 (m, 3H), 4.74 (m, 1H), 3.68 (br.s, 1H, NH), 2.84-2.89 (m, 1H), 2.70-2.79 (m, 1H), 2.28-2.32 (m, 1H), 1.85-1.96 (m, 1H), 1.76-1.80 (m, 1H), 1.58-1.66 (m, 1H).

Example 6

Intermediate N-phenyl-8-(4,4,5,5-tetramethyl-1,3,2-dioxaborolan-2-yl)-1,2,3,4-tetrahydronaphthalen-1-amine

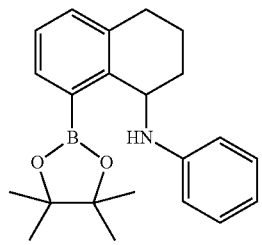 [SMILES: CC1(C)OB(c2cccc3c2C(Nc2ccccc2)CCC3)OC1(C)C]

Tetrahydrofuran (1,000 mL) and (8-bromo-1,2,3,4-tetrahydronaphthalen-1-yl)phenylamine (37.6 g, 124 mmol) were combined and cooled to −80° C. Then a 2.5 M solution of n-BuLi (49.7 mL, 124 mmol) in hexanes was added, and the resulting reaction mixture was stirred for 1 hour at −80° C. Then, a 1.9 M solution of t-BuLi (137 mL, 260 mmol) in pentane was added, and the resulting mixture was stirred for 1 hour at −80° C. To the mixture was then added 2-isopropoxy-4,4,5,5-tetramethyl-1,3,2-dioxaborolane (48.4 g, 260 mmol). The cooling bath was then removed, and the resulting mixture was stirred for 1 hour at room temperature. Water (50 mL) was then added, and the obtained mixture was evaporated to dryness. The residue was diluted with water (500 mL), and the crude product was extracted with of ethyl acetate (3×300 mL). The combined organic extracts were dried over Na₂SO₄ and then evaporated to dryness. Yield 43.3 g (quant.) of a red oil. ¹H NMR (CDCl₃): δ 7.59 (m, 1H), 7.18-7.23 (m, 4H), 6.71-6.74 (m, 3H), 5.25 (m, 1H), 3.87 (br.s, 1H, NH), 2.76-2.90 (m, 2H), 2.12-2.16 (m, 1H), 1.75-1.92 (m, 3H), 1.16 (s, 6H), 1.10 (s, 6H).

Example 7

Intermediate 8-(2,6-diisopropylphenylamino)quinolin-2(1H)-one

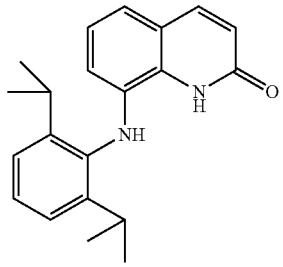 [SMILES: CC(C)c1cccc(C(C)C)c1Nc1cccc2ccc(=O)[nH]c12]

To a stirred suspension of NaH (60% in mineral oil, 5.63 g, 140 mmol) in dry THF (1,000 mL) was added 8-bromo-quinolin-2(1H)-one (30.0 g, 134 mmol) in small portions at 0° C. After the addition was completed, the mixture was warmed to room temperature for 30 minutes. The solution obtained was then cooled to 0° C., and tert-butyl-dimethyl-silylchloride (TBDMSCl) (20.2 g, 134 mmol) was added in one portion. After 30 minutes of stirring at room temperature the resulting mixture was poured into water (1,000 mL). The protected 8-bromoquinolin-2(1H)-one was extracted with diethyl ether (3×400 mL). The combined extracts were dried over Na$_2$SO$_4$ and then evaporated to dryness. Yield 45.2 g (quant., 99% purity by GC/MS) of a dark red oil. To a solution of 2,6-diisopropylaniline (27.7 mL, 147 mmol) in dry toluene (1,500 mL) was added n-BuLi (60.5 mL, 147 mmol, 2.5 M in hexanes) at room temperature. The obtained suspension was heated to 100° C. and then cooled to room temperature. To this reaction mixture were added Pd$_2$(dba)$_3$ (dba=dibenzylideneacetone, 2.45 g, 2.68 mmol) and 2-dicyclohexylphosphino-2',4',6'-triisopropylbiphenyl (XPhos, 2.55 g, 5.36 mmol). Then the protected 8-bromoquinolin-2 (1H)-one (45.2 g, 134 mmol) was also added to the solution. The formed dark brown suspension was heated at 60° C. until the lithium salt precipitate dissolved (ca. 30 min). The resulting dark red solution was quenched by the addition of water (100 mL), and the organic layer was separated, dried over Na$_2$SO$_4$, and then evaporated to dryness. The oily residue obtained was dissolved in a mixture of dichloromethane (1,000 mL) and methanol (500 mL), followed by an addition of 12 M hydrochloric acid (50 mL). The reaction mixture was stirred at room temperature for 3 hours, then poured into an aqueous solution of 5% K$_2$CO$_3$ (2000 mL). The product was extracted with dichloromethane (3×700 mL). The combined extracts were dried over Na$_2$SO$_4$ and then evaporated to dryness. The resulting solid was triturated with n-hexane (300 mL) to cause the formation of a suspension. The solid was isolated by filtration on a glass frit (G3) and dried under reduced pressure. Yield 29.0 g (67%) of a marsh-green solid. $^1$H NMR (CDCl$_3$): δ 13.29 (br.s, 1H), 7.80-7.81 (d, 1H, J=9.5 Hz), 7.35-7.38 (m, 1H), 7.29-7.30 (m, 3H), 6.91-6.95 (m, 2H), 6.58-6.60 (d, 1H, J=9.5 Hz), 6.27-6.29 (m, 1H), 3.21 (sept, 2H, J=6.9 Hz), 1.25-1.26 (d, 6H, J=6.9 Hz), 1.11-1.12 (d, 6H, J=6.9 Hz).

Example 8

Intermediate
2-chloro-N-(2,6-diisopropylphenyl)quinolin-8-amine

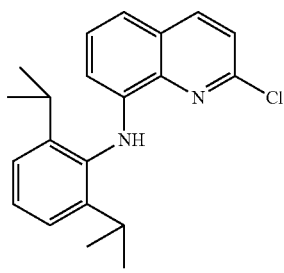 [SMILES: CC(C)c1cccc(C(C)C)c1Nc1cccc2ccc(Cl)nc12]

8-(2,6-Diisopropylphenylamino)quinolin-2(1H)-one (29.0 g, 90.6 mmol) was added to phosphorus oxychloride (400 mL, 4.3 mol) in one portion. The resulting suspension was heated at 105° C. for 40 hours, then cooled to room temperature, and poured into crushed ice (4 L). The product was extracted with diethyl ether (3×400 mL). The combined extracts were dried over K$_2$CO$_3$ and then evaporated to dryness. The resulting solid was triturated with cold n-hexane (30 mL), and the obtained suspension was collected by filtration on a fritted disk. The obtained precipitate was dried in vacuum. Yield 29.0 g (95%) of a yellow-green solid. $^1$H NMR (CDCl$_3$): δ 8.04-8.05 (d, 1H, J=8.6 Hz), 7.38-7.39 (d, 1H, J=8.5 Hz), 7.33-7.36 (m, 1H), 7.22-7.27 (m, 4H), 7.04-7.06 (d, 1H, J=8.1 Hz), 6.27-6.29 (d, 1H, J=7.8 Hz), 3.20 (sept, 2H, J=6.9 Hz), 1.19-1.20 (d, 6H, J=6.9 Hz), 1.10-1.11 (d, 6H, J=6.9 Hz).

Example 9

Ligand 2-(8-anilino-5,6,7,8-tetrahydronaphthalen-1-yl)-N-(2,6-diisopropylphenyl)quinolin-8-amine

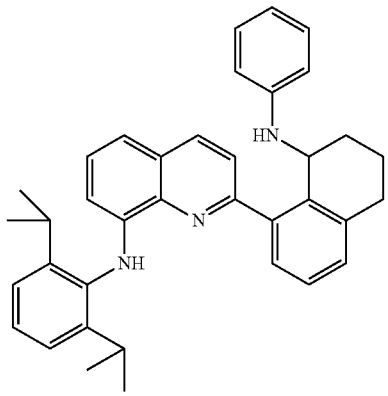 [SMILES: CC(C)c1cccc(C(C)C)c1Nc1cccc2ccc(-c3cccc4c3C(Nc3ccccc3)CCC4)nc12]

To a solution of 2-chloro-N-(2,6-diisopropylphenyl)quinolin-8-amine (37.5 g, 110 mmol) in 1,4-dioxane (1,500 mL), were added N-phenyl-8-(4,4,5,5-tetramethyl-1,3,2-dioxaborolan-2-yl)-1,2,3,4-tetrahydronaphthalen-1-amine (39.5 g, 113 mmol), cesium carbonate (89.5 g, 275 mmol), and water (800 mL). The resulting mixture was purged with argon for 10 minutes followed by an addition of Pd(PPh$_3$)$_4$ (6.36 g, 5.50 mmol). This mixture was stirred for 2 hours at 90° C., then cooled to room temperature. To the obtained two-phase mixture was added n-hexane (1,000 mL). The organic layer was separated, washed with brine, dried over Na$_2$SO$_4$, passed through a short pad of silica gel 60 (to remove traces of triphenylphosphine oxide), and then evaporated to dryness. The residue was re-crystallized from n-hexane (450 mL). Yield 45.4 g (78%) of a lemon-yellow powder. Anal. calc. for C$_{37}$H$_{39}$N$_3$: C, 84.53; H, 7.48; N, 7.99. Found: C, 84.70; H, 7.33; N, 8.15. $^1$H NMR (CDCl$_3$): δ 7.88 (d, J=8.3 Hz, 1H), 7.60 (s, 1H), 7.47 (d, J=8.4 Hz, 1H), 7.34-7.42 (m, 3H), 7.25-7.34 (m, 3H), 7.16 (t, J=7.8 Hz, 1H), 6.91 (d, J=8.1 Hz, 1H), 6.77 (t, J=7.6 Hz, 2H), 6.39 (t, J=7.2 Hz, 1H), 6.24 (d, J=7.6 Hz, 1H), 6.18 (d, J=8.1 Hz, 2H), 5.39 (br. s., 1H), 3.59 (br. s., 1H), 3.35-3.51 (m, 1H), 3.23-3.33 (m, 1H), 2.95-3.07 (m, 1H), 2.85-2.95 (m, 1H), 2.15 (d, J=12.3 Hz, 1H), 1.88-1.99 (m, 1H), 1.77-1.88 (m, 2H), 1.22-1.41 (m, 6H), 1.12-1.21 (m, 6H).

Example 10

2-(8-anilino-5,6,7,8-tetrahydronaphthalen-1-yl)-N-(2,6-diisopropylphenyl)quinolin-8-amido-dimethyl-hafnium Catalyst Complex, QDA-Hf(Me)$_2$

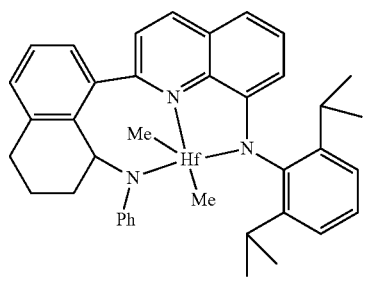

Toluene (80 mL) was added to 2-(8-anilino-5,6,7,8-tetra-hydronaphthalen-1-yl)-N-(2,6-diisopropylphenyl)quinolin-8-amine (5.500 g, 10.46 mmol) and Hf(NMe$_2$)$_4$ (3.865 g, 10.89 mmol) to form a clear orange solution after stirring for few minutes. The mixture was placed on a metal block that was then warmed to 85° C. After 21 hours, the solution was clear and red tinted. The flask was allowed to cool to near ambient temperature and AlMe$_3$ (5.279 g, 73.23 mmol) was added quickly. The mixture became a darker red. After 7 hours the volatiles were removed overnight by evaporation with a stream of nitrogen. The resulting orange solid was crushed with a spatula and toluene (5 mL) was added to form a slurry. The slurry was stirred for 30 minutes then pentane (60 mL) was added. The suspension was stirred for 3 hours. The solid was then collected on a frit and washed with cold pentane (2×30 mL) to afford the product as an orange solid. $^1$H NMR spectroscopic data illustrated in FIG. 1 indicates that the product was pure. Yield 6.93 g (90.5%).

Example 11

Intermediate 6-nitro-2,3-dihydro-1H-inden-1-one

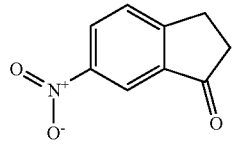 [SMILES: O=C1CCc2ccc([N+](=O)[O-])cc21]

To cold 98% sulfuric acid (500 mL) was added 2,3-dihydro-1H-inden-1-one (66.0 g, 500 mmol) portionwise over 30 minutes at −10° C. Then, a solution of KNO$_3$ (75.8 g, 0.75 mol) in 98% sulfuric acid (250 mL) was added dropwise to the above mixture over 2 hours at −10° C. The resulting mixture was stirred for 30 minutes at −10° C. The obtained mixture was poured into a mixture of crushed ice (2 kg) and cold water (2 L). The formed yellowish precipitate was filtered off and washed with water (5×300 mL) and ethanol (100 mL). The precipitate was air-dried overnight to give 68.0 g (77%) of a ca. 3:1 mixture of 6-nitro-2,3-dihydro-1H-inden-1-one and 4-nitro-2,3-dihydro-1H-inden-1-one as a yellow powder. $^1$H NMR (CDCl$_3$): δ 8.54 (d, J=1.9 Hz, 1H), 8.43 (dd, J=8.4, 2.1 Hz, 1H), 7.65 (d, J=8.3 Hz, 1H), 3.22-3.32 (m, 2H), 2.79-2.86 (m, 2H).

Example 12

Intermediate 6-amino-2,3-dihydro-1H-inden-1-one

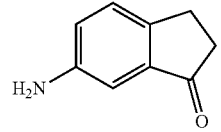 [SMILES: Nc1ccc2c(c1)C(=O)CC2]

The mixture of nitroindanones (47.6 g, 270 mmol) from the previous step were combined with 95% ethanol (800 mL). To this solution was added SnCl$_2$.H$_2$O (300 g, 1.34 mol) in one portion. The resulting mixture was heated to reflux for 2 hours. Then, a solution of NaOH (90 g) in water (900 mL) was added portionwise to form a suspension (with pH=8-9). This suspension was divided into two parts, and each of them was extracted with diethyl ether (3×300 mL). The combined organic extract was washed with water, dried over Na$_2$SO$_4$, and passed through a pad of silica gel 60 (40-63 m, 100 mL). The obtained elute was evaporated to dryness to give 20.0 g (50%, a ca. 3:1 mixture of the respective aminoindanones) of a dark brown crystalline solid. $^1$H NMR (CDCl$_3$): δ 7.23 (d, J=8.1 Hz, 1H), 6.95-6.99 (m, 1H), 6.90-6.95 (m, 1H), 3.81 (br. s., 2H), 2.91-3.04 (m, 2H), 2.57-2.66 (m, 2H).

Example 13

Intermediate 6-amino-7-bromo-2,3-dihydro-1H-inden-1-one

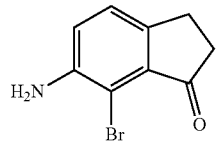 [SMILES: Nc1ccc2c(c1Br)C(=O)CC2]

The mixture of aminoindanones (20.0 g, 136 mmol) from the previous step were combined with N,N-dimethylformamide (400 mL). To this solution was added dropwise a solution of N-bromosuccinimide (23.7 g, 133 mmol) in N,N-dimethylformamide (200 mL) over 2 hours at 0° C. The resulting mixture was stirred for 1 hour and then poured into water (1 L). The crude product was extracted with dichloromethane (3×300 mL), and the combined extract was washed with water (3×500 mL). Further on, the organic phase was dried over Na$_2$SO$_4$, passed through a silica gel pad (100 mL), and the elute was evaporated to dryness to give 25.3 g (82%) of a ca. 3:2 mixture of 6-amino-7-bromo-2,3-dihydro-1H-inden-1-one and 4-amino-7-bromo-2,3-dihydro-1H-inden-1-one as a dark brown crystals. $^1$H NMR (CDCl$_3$): 7.27 (d, J=8.3 Hz), 7.13-7.20 (n, J=8.2 Hz), 6.94-7.02 (m, J=8.1 Hz), 6.70 (d, J=8.3 Hz), 4.12 (br.s.), 2.90-2.97 (m), 2.65-2.82 (m).

Example 14

Intermediate 7-bromo-2,3-dihydro-1H-inden-1-one

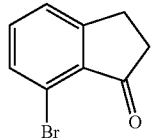 [SMILES: O=C1CCc2cccc(Br)c21]

To cold 4 M HCl (140 mL) was added the mixture of amino-bromoindanones (25.3 g, 112 mmol) from the previous step in one portion at 3° C. Then a solution of NaNO$_2$ (8.49 g, 123 mmol) in water (80 mL) was added dropwise over 1 hour at 3° C. Then H$_3$PO$_2$ (50% in water, 118 mL, 1.12 mol) was added dropwise at 5° C. over 30 minutes. The resulting mixture was diluted with water (500 mL) and extracted with dichloromethane (3×200 mL). The combined organic extract was dried over Na$_2$SO$_4$, passed through a pad of silica gel 60 (40 μm-63 m, 100 mL) and evaporated to dryness. The residue was recrystallized from hexane-ethyl acetate mixture (2:1, v/v) and dried in vacuum. Yield 18.9 g (80%) of a colorless crystalline solid. $^1$H NMR (CDCl$_3$): δ 7.47-7.51 (m, 1H), 7.33-7.43 (m, 2H), 3.04-3.11 (m, 2H), 2.67-2.74 (m, 2H).

Example 15

Intermediate N-(2-bromophenyl)cinnamamide

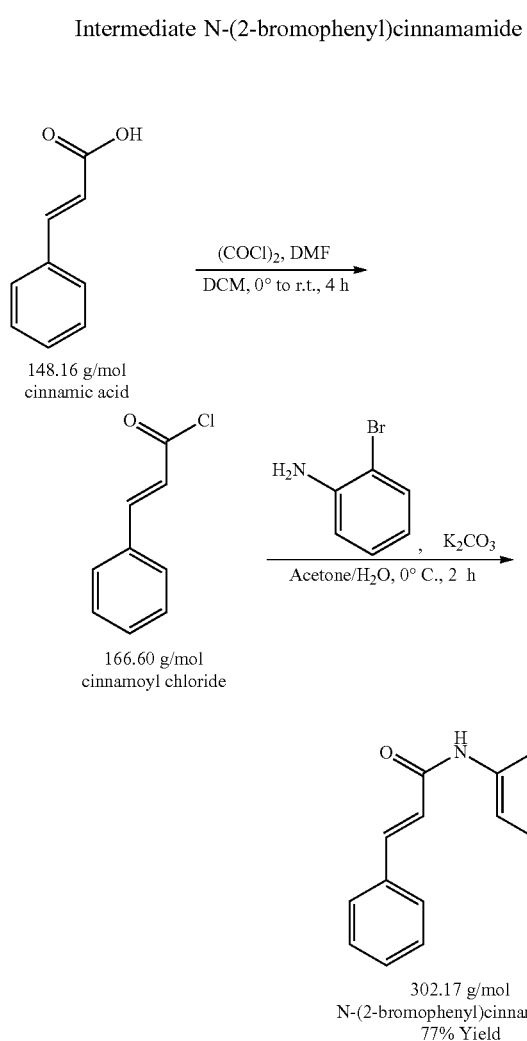

A mixture of cinnamic acid (134.99 mmol) and dimethylformamide (13.50 mmol, 1.0 mL) in 250 mL of dichloromethane was stirred for 5 minutes. After cooling to 0° C., oxalyl chloride (202.48 mmol) was added dropwise and the mixture was allowed to stir for 4 hours at room temperature. The solvent was removed under vacuum. The resulting cinnamoyl chloride was combined with 2-bromoaniline (134.99 mol) in 170 mL of acetone/water (7:10 ratio) and was stirred for 2 hours at 0° C. The reaction mixture was put under a stream of nitrogen to remove acetone then poured into ice water (150 mL) and the resulting beige colored precipitate was collected via vacuum filtration and washed with hot hexane (150 mL) giving a yellow-brown filtrate and a slightly off-white precipitate. The solid precipitate was taken up in hot hexane and stirred for 20 minutes. The white solid was collected via vacuum filtration. Yield: 31.30 g (77%).

Example 16

Intermediate 8-bromoquinolin-2(1H)-one

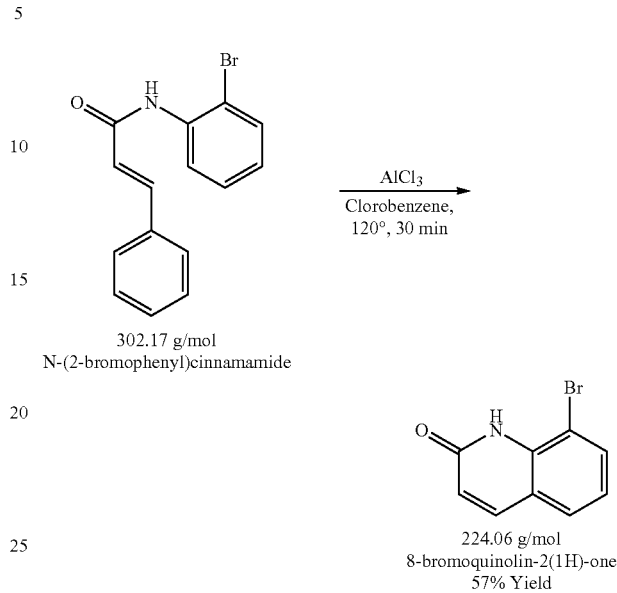

To a solution of N-(2-bromophenyl)cinnamamide (67.18 mmol) in chlorobenzene (75 mL), aluminum chloride (335.90 mmol) was added incrementally. The mixture was brought to 120° C. then stirred for 30 minutes. The reaction solution was cooled to 50° C., poured over ice water (200 mL) and the solid was collected via vacuum filtration. The filtrate was placed in the refrigerator and a second crop of crystals was collected. Product residue was triturated with ethanol (100 mL) for 20 minutes then collected via vacuum filtration and placed under vacuum overnight. Yield: 8.62 g (57%).

Example 17

Intermediate 8-bromo-2-((tert-butyldimethylsilyl)oxy)-1,2-dihydroquinoline

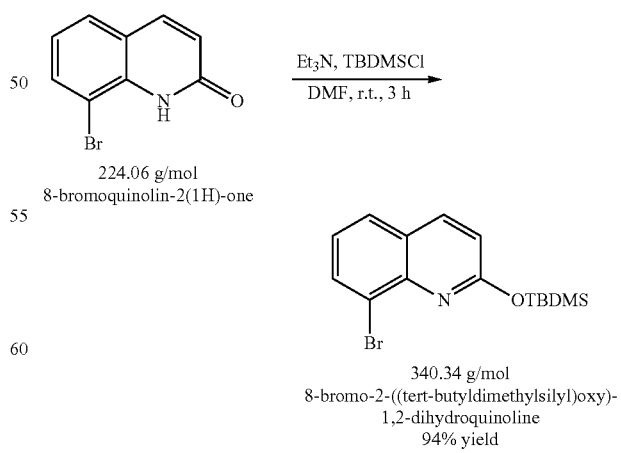

At room temperature, tert-butyldimethylsilyl chloride (76.93 mmol) was added to a stirring solution of 8-bromoquinolin-2(1H)-one (38.47 mmol) in dimethylformamide (300 mL). This was followed by addition of triethylamine (135 mmol, 20 mL). The reaction mixture was allowed to stir for 3 hours, then poured into cold water (500 mL) and extracted with diethyl ether (3×150 mL). The organic layer was washed with water (3×150 mL), dried (MgSO$_4$), filtered and concentrated under vacuum. Yield: 12.33 g (94%).

Example 18

Intermediate 2-((tert-butyldimethylsilyl)oxy)-N-(2,6-diisopropylphenyl)quinolin-8-amine

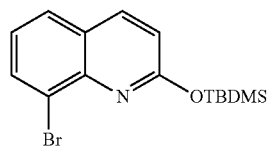

338.32 g/mol
8-bromo-2-((tert-butyldimethylsilyl)oxy)quinoline

+

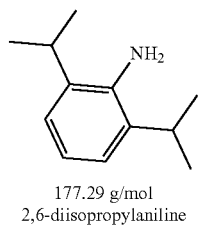

177.29 g/mol
2,6-diisopropylaniline nBuLi, Pd$_2$(dba)$_3$, XPhos
toluene, r.t. to 100° C. to r.t.
add cat.; incr. to 60° C.;
stir until Li salt dissolves

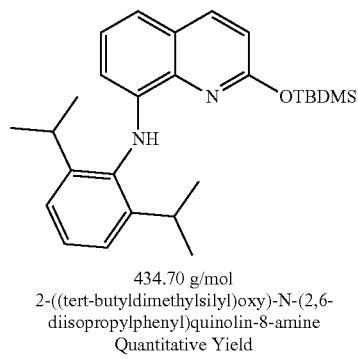

434.70 g/mol
2-((tert-butyldimethylsilyl)oxy)-N-(2,6-diisopropylphenyl)quinolin-8-amine
Quantitative Yield At room temperature, 1.6M n-BuLi (33.16 mmol, 20.7 mL) was added to a solution of 2,6-diisopropylaniline (33.16 mmol) in toluene (300 mL). The mixture was heated to 100° C. then cooled to room temperature. Tris(dibenzylideneacetone)dipalladium(0) (0.60 mmol) and then Xphos (1.21 mmol) were added to the reaction mixture followed by 8-bromo-2-((tert-butyldimethylsilyl)oxy)quinoline (30.15 mmol), and the reaction was heated to 60° C. until the lithium salt precipitate disappeared (approximately 30 min). The resulting dark red solution was quenched with water (200 mL). The organic layer was separated, dried (MgSO$_4$), filtered and concentrated. The residue was passed through a silica plug (25% ethyl acetate/hexane), then dried, filtered and concentrated in vacuo. Yield: 13.11 g (quantitative).

Example 19

Intermediate 8-((2,6-diisopropylphenyl)amino)quinolin-2(1H)-one

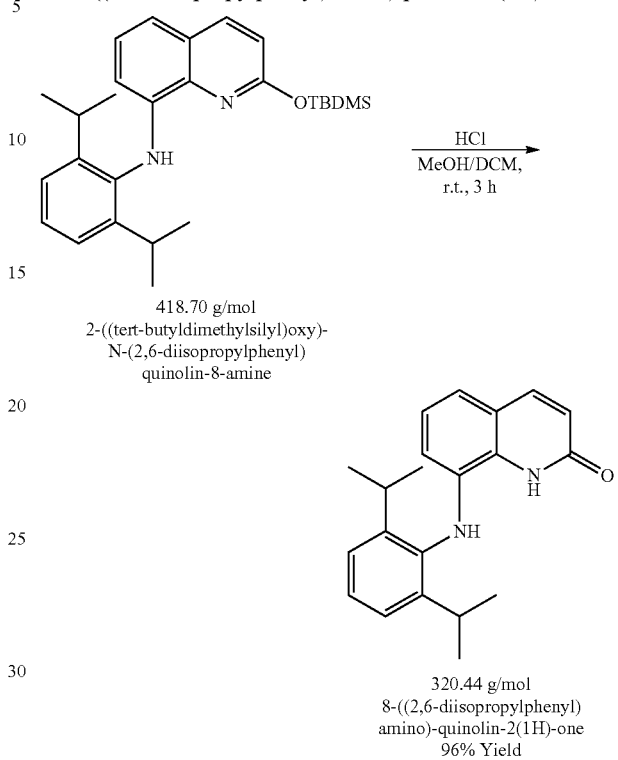

418.70 g/mol
2-((tert-butyldimethylsilyl)oxy)-N-(2,6-diisopropylphenyl)quinolin-8-amine HCl
MeOH/DCM,
r.t., 3 h 320.44 g/mol
8-((2,6-diisopropylphenyl)amino)-quinolin-2(1H)-one
96% Yield At room temperature, 12M hydrochloric acid (188.43 mmol, 15.7 mL) was added to a mixture of 2-(tert-butyldimethylsilyl)-N-(2,6-diisopropylphenyl)quinolin-8-amine (31.4 mmol) dissolved in dichloromethane (300 mL) and methanol (150 mL). The reaction mixture was stirred for 3 hours, then poured into a saturated potassium carbonate solution (500 mL) then extracted with dichloromethane (3×150 mL). The combined organic fractions were dried (MgSO$_4$), filtered and concentrated in vacuo. Yield: 9.65 g (96%).

Example 20

Intermediate 2-chloro-N-(2,6-diisopropylphenyl)quinolin-8-amine

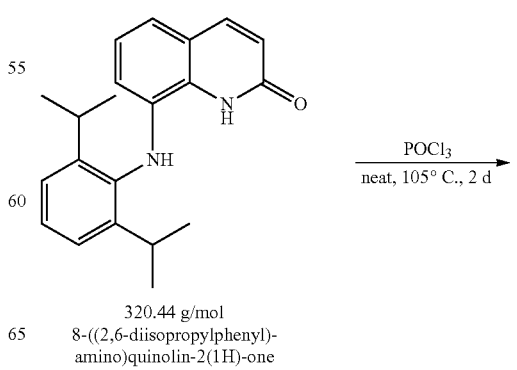

320.44 g/mol
8-((2,6-diisopropylphenyl)-amino)quinolin-2(1H)-one

POCl$_3$
neat, 105° C., 2 d

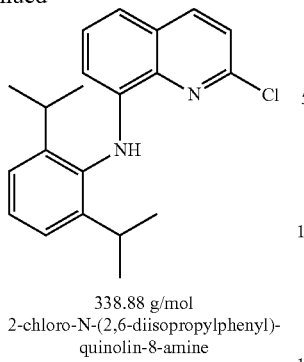

338.88 g/mol
2-chloro-N-(2,6-diisopropylphenyl)-
quinolin-8-amine
92% Yield

In the drybox, 8-((2,6-diisopropylphenyl)amino)quinolin-2(1H)-one (30.12 mmol) was added to Phosphoryl chloride (602.30 mmol, 56 mL) at room temperature. The mixture was stirred at 105° C. for 2 days. The reaction mixture was brought to room temperature and poured over 150 mL of crushed ice. The crude product was extracted with diethyl ether (3×50 mL) and the combined organic extracts were dried (MgSO₄), filtered and concentrated under a stream of nitrogen. The resulting solid was recrystallized from hexane. The precipitate was collected via vacuum filtration. Yield: 9.36 g (92%).

Example 21

Intermediate
8-bromo-1,2,3,4-tetrahydronaphthalen-1-ol

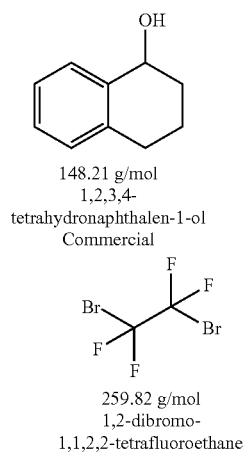

At 0° C., 1.6M n-BuLi (35.42 mmol, 22.14 mL) was added dropwise to 1,2,3,4-tetrahydronaphthalen-1-ol (16.87 mmol) and N,N,N'N'-tetramethylethylenediamine (TMEDA) (33.74 mmol) in pentane (100 mL). The solution was brought to reflux (40° C.) and stirred overnight. The reaction solution was brought to 0° C. and 1,2-dibromo-1,1,2,2-tetrafluoroethane (16.87 mmol) was added dropwise to the stirring solution. The mixture was allowed to come to room temperature and stirred for 3 days. The mixture was washed with saturated ammonium chloride solution (50 mL) and then saturated sodium carbonate solution (50 mL). The organic layer was collected, dried (MgSO₄), filtered and concentrated. The residue was purified via column chromatography (stationary phase: silica gel; eluent: 10%-20% ethyl acetate/hexane). Yield: 2.14 g (56%).

Example 22

Intermediate
8-bromo-3,4-dihydronaphthalen-1(2H)-one

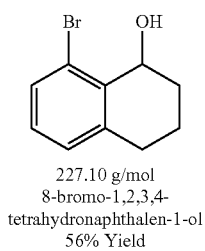

227.10 g/mol
8-bromo-1,2,3,4-tetrahydronaphthalen-1-ol 225.09 g/mol
8-bromo-3,4-dihydronaphthalen-1(2H)-one
95% Yield Pyridinium chlorochromate (PCC) (64.29 mmol) was added to a stirring solution of 8-bromo-1,2,3,4-tetrahydronaphthalen-1-ol (12.86 mmol) in dichloromethane (150 mL). The reaction mixture was passed through a silica plug and solvent was removed in vacuo. Yield: 2.76 g (95%).

Example 23

Intermediate (E)-8-bromo-N-(4-hexylphenyl)-3,4-dihydronaphthalen-1(2H)-imine

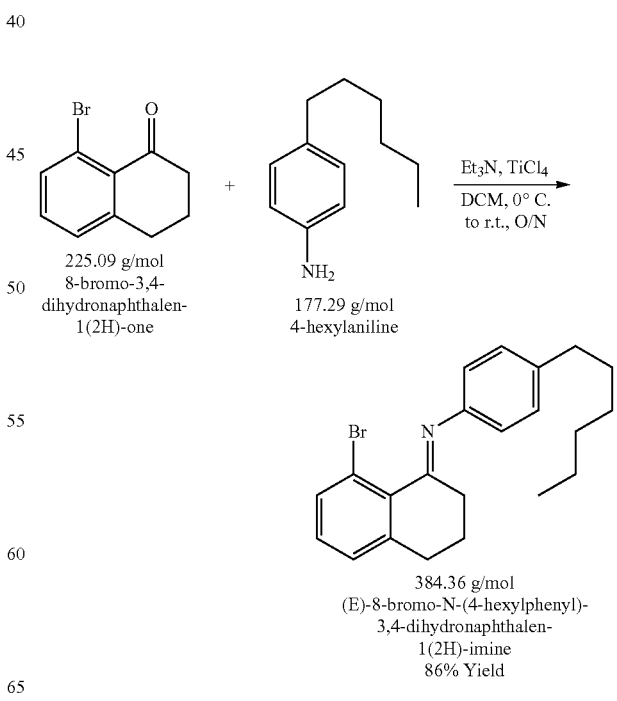

225.09 g/mol
8-bromo-3,4-dihydronaphthalen-1(2H)-one 177.29 g/mol
4-hexylaniline 384.36 g/mol
(E)-8-bromo-N-(4-hexylphenyl)-3,4-dihydronaphthalen-1(2H)-imine
86% Yield 86% Yield A solution of 8-bromo-3,4-dihydronaphthalen-1(2H)-one (6.66 mmol), 4-hexylaniline (10.00 mmol), and triethylamine (13.33 mmol, 2 mL) in dichloromethane (20 mL) was brought to 0° C. Titanium(IV) chloride (19.99 mmol) in dichloromethane (5 mL) was added dropwise to the stirring solution, and the reaction mixture was allowed to come to room temperature and stirred overnight. The reaction mixture was poured into saturated potassium carbonate solution (25 mL) and organics were extracted with diethyl ether (3×20 mL). Combined organic layers were washed with brine, dried (MgSO$_4$), filtered and concentrated under vacuum. Yield: 2.20 g (86%).

Example 24

Intermediate 8-bromo-N-(4-hexylphenyl)-1,2,3,4-tetrahydronaphthalen-1-amine

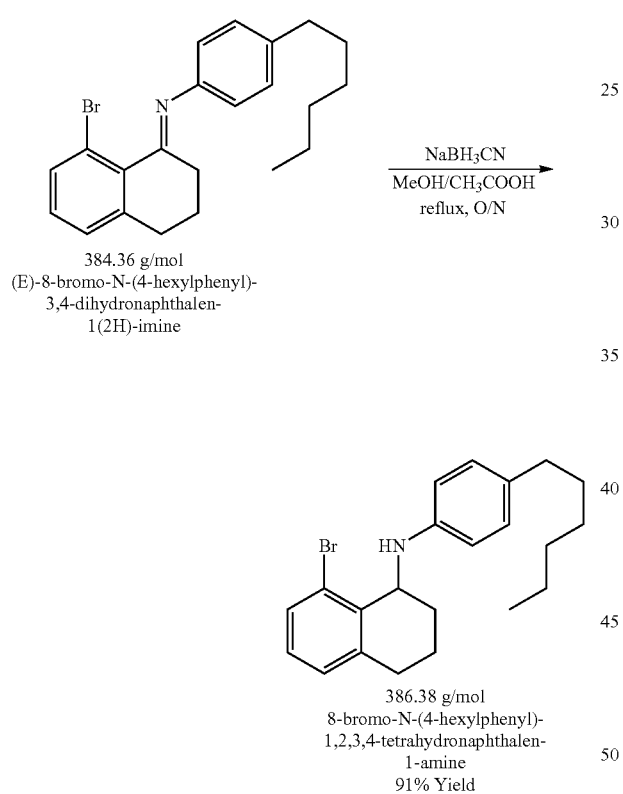

Sodium cyanoborohydride (11.12 mmol) was added to a stirring solution of (E)-8-bromo-N-(4-hexylphenyl)-3,4-dihydronaphthalen-1 (2H)-imine (7.42 mmol) in methanol (25 mL) and glacial acetic acid (3 mL). The reaction was brought to reflux (65° C.) and stirred overnight. The reaction mixture was allowed to come to room temperature and solvent was removed under vacuum. The residue was diluted with 50 mL of water then extracted with ethyl acetate (3×50 mL). The combined organic layers were dried (MgSO$_4$), filtered and concentrated. Yield: 2.62 g (91%).

Example 25: Borylation at 0° C.

Intermediate N-(4-hexylphenyl)-8-(4,4,5,5-tetramethyl-1,3,2-dioxaborolan-2-yl)-1,2,3,4-tetrahydronaphthalen-1-amine

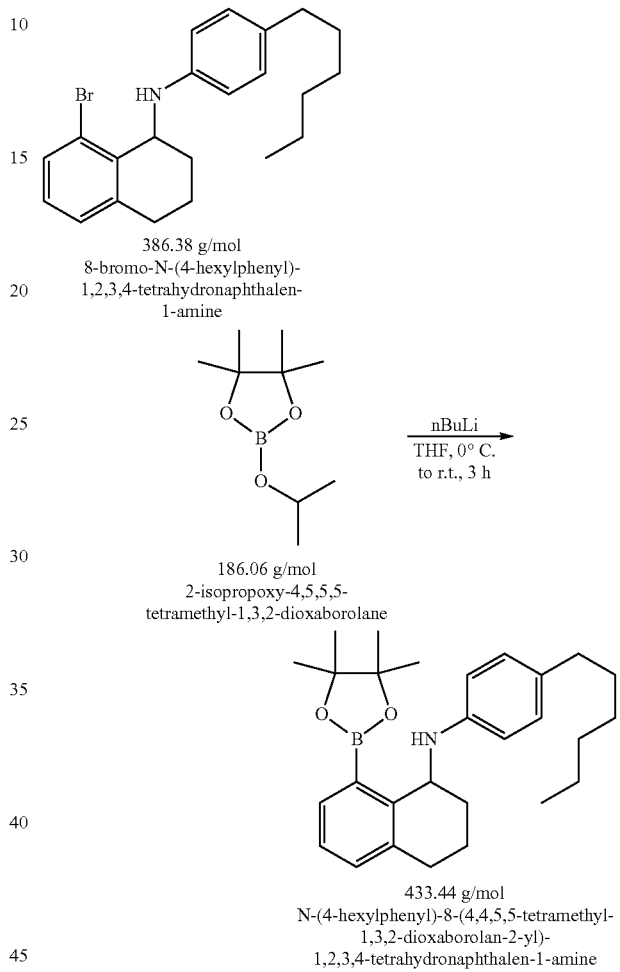

At 0° C., n-butyllithium (3 eq., 2.205 mmol, 1.4 mL of a 1.6M solution) was added to a solution of 8-bromo-N-(4-hexylphenyl)-1,2,3,4-tetrahydronaphthalen-1-amine (1 eq., 0.735 mmol, 0.284 g) in tetrahydrofuran (6 mL). This was stirred for 15 min. then brought back to 0° C. after which 2-isopropoxy-4,4,5,5-tetramethyl-1,3,2-dioxaborolane (2.0 eq., 1.470 mmol, 0.3 mL) was added to the stirring solution. The reaction was stirred at room temperature for 3 hours. The reaction mixture was poured into water (10 mL) and extracted with ethyl acetate (3×5 mL). The combined organic fractions were dried (MgSO$_4$), filtered and concentrated under a stream of nitrogen overnight. The crude mixture was then purified via column chromatography (silica gel, 60-80% dichloromethane/hexane). 0.110 g, 0.254 mmol (34.5% yield) of clean, desired product was recovered.

Comparative Example: 8-(4,4,5,5-Tetramethyl-1,3,2-dioxaborolan-2-yl)-3,4-dihydronaphthalen-1(2H)-one

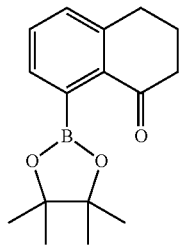 [SMILES: CC1(C)OB(c2cccc3c2C(=O)CCC3)OC1(C)C]

A mixture of 8-bromo-3,4-dihydronaphthalen-1(2H)-one (2.25 g, 10.0 mmol), 4,4,4',4',5,5,5',5'-octamethyl-2,2'-bi(1,3,2-dioxaborolane (2.79 g, 11.0 mmol), potassium acetate (2.94 g, 30.0 mmol), dppf (0.28 g, 0.50 mmol, dppf=(1,1'-ferrocenediyl-bis(diphenylphosphine), and Pd$_2$(dba)$_3$ (0.46 g, dba=dibenzylideneacetone), and 1,4-dioxane (60 mL) was stirred in argon atmosphere for 12 hours at 95° C. Then, the mixture was cooled to room temperature and poured into water (300 mL). The obtained mixture was extracted with dichloromethane (3×100 mL). The combined organic extract was washed with saturated NaHCO$_3$(100 mL), dried over Na$_2$SO$_4$, and then evaporated to dryness. The residue was purified by flash chromatography on silica gel 60 (40-63 μm, eluent: hexane-ethyl acetate=10:1, vol.). Yield 1.80 g (66%) of orange crystalline solid. $^1$H NMR (CDCl$_3$): δ 7.40-7.44 (m, 1H), δ 7.29-7.33 (m, 1H), δ 7.18-7.22 (m, 1H), 2.91 (t, J=6.1 Hz, 2H), δ 2.64-2.69 (m, 2H), 2.11 (td, J=6.4, J=12.6 Hz, 2H), 1.44 (s, 12H).

Comparative Example: 8-(8-((2,6-Diisopropylphenyl)amino)quinolin-2-yl)-3,4-dihydronaphthalen-1(2H)-one

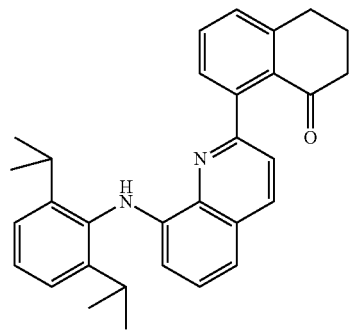 [SMILES: CC(C)c1cccc(C(C)C)c1Nc1cccc2ccc(-c3cccc4c3C(=O)CCC4)nc12]

1,4-dioxane (100 mL) was combined with 2-chloro-N-(2,6-diisopropylphenyl)quinolin-8-amine (2.24 g, 6.61 mmol) to form a solution. To this solution were subsequently added 8-(4,4,5,5-tetramethyl-1,3,2-dioxaborolan-2-yl)-3,4-dihydronaphthalen-1(2H)-one (1.80 g, 6.61 mmol), cesium carbonate (6.46 g, 19.8 mmol), and water (50 mL). The obtained mixture was purged with argon followed by an addition of Pd(PPh$_3$)$_4$ (0.38 g, 0.33 mmol). This mixture was stirred for 12 hours at 95° C., then cooled to room temperature and poured into water (300 mL). The obtained mixture was extracted with dichloromethane (3×100 mL). The combined organic extract was dried over Na$_2$S$_{O4}$ and then evaporated to dryness. The residue was purified by flash chromatography on silica gel 60 (40-63 μm, eluent: hexane-dichloromethane=1:1, vol.). Yield: 2.00 g (68%) of orange oil. $^1$H NMR (CDCl$_3$): δ 8.05 (d, J=8.5 Hz, 1H), 7.52-7.76 (m, 2H), 7.39-7.44 (m, 2H), 7.29-7.36 (m, 2H), 7.19-7.23 (m, 2H), 7.07-7.09 (m, 2H), 6.23 (dd, J=7.6 Hz, J=0.8 Hz, 1H), 3.25 (sept, J=6.9 Hz, 2H), 3.06 (t, J=6.0 Hz, 2H), 2.68 (t, J=6.7 Hz, 2H), 2.20 (qd, J=6.4, 6.5 Hz, 2H), 1.13 (t, J=6.7 Hz, 12H).

Comparative Example: 2-(8-(Cyclododecylamino)-5,6,7,8-tetrahydronaphthalen-1-yl)-N-(2,6-diisopropylphenyl)quinolin-8-amine

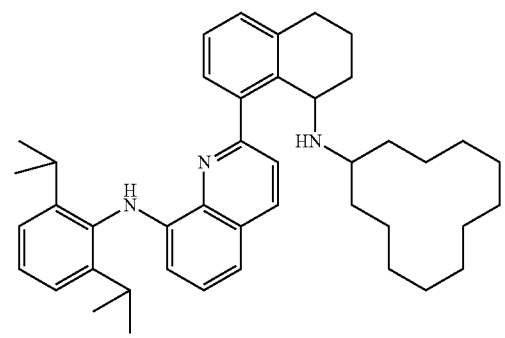 [SMILES: CC(C)c1cccc(C(C)C)c1Nc1cccc2ccc(-c3cccc4c3C(NC3CCCCCCCCCCC3)CCC4)nc12]

A solution of 8-(8-((2,6-diisopropylphenyl)amino)quinolin-2-yl)-3,4-dihydronaphthalen-1(2H)-one (2.00 g, 4.46 mmol), titanium (IV) isopropoxide (3.84 g, 13.3 mmol) and anhydrous toluene (25 mL) was stirred in argon atmosphere for 12 hours at 100° C. The mixture was then cooled to room temperature and diluted with anhydrous MeOH (100 mL) followed by an addition of acetic acid (8 mL) and NaBH$_3$CN (0.86 g, 8.92 mmol). The obtained mixture was stirred for 3 hours at 60° C., then it was cooled to room temperature and poured into a mixture of water (300 mL) and dichloromethane (100 mL). The resulting mixture was filtered through a short pad of Celite 503, which was thoroughly washed with dichloromethane (200 mL). The organic phase was separated, washed with saturated NaHCO$_3$(200 mL), dried over Na$_2$SO$_4$ and evaporated to dryness. The residue was purified by flash chromatography on silica gel 60 (40-63 μm, eluent: hexane-ethyl acetate=5:1, vol.). Yield: 1.40 g (51%). $^1$H NMR (CDCl$_3$): δ 8.16 (d, J=8.4 Hz, 1H), 7.54-7.57 (m, 2H), 7.15-7.34 (m, 6H) 7.09 (dd, J=1.0, J=8.1 Hz, 1H), 6.25 (dd, J=1.0, J=7.7 Hz, 1H), 4.65 (br.s., 1H), 3.19-3.28 (m, 2H), 2.82-2.98 (m, 2H), 2.28-2.31 (m, 1H), 1.97-2.15 (m, 2H), 1.62-1.75 (m, 2H), 0.79-1.53 (m, 31H), 0.70-0.79 (m, 1H), 0.44-0.62 (m, 2H), 0.31-0.41 (m, 1H), 0.14-0.23 (m, 1H).

Overall, methods of the present disclosure can provide syntheses of quinolinyldiamines (and catalysts thereof) providing economic and scale-up advantages for commercial-scale applicability due in-part to the reduction or elimination of column chromatography used in the syntheses of the quinolinyldiamines and or intermediates thereof.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the present disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While the present disclosure has been described with respect to a number of embodiments and examples, those skilled in the art, having benefit of this disclosure, will appreciate that other embodiments can be devised which do not depart from the scope and spirit of the present disclosure.

What is claimed is:
1. A method for making a quinolinyldiamine represented by Formula (I):

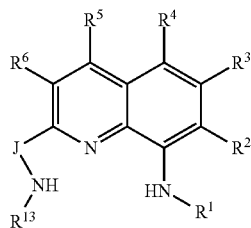

(I)

wherein:
$R^1$ and $R^{13}$ are independently selected from hydrocarbyl, substituted hydrocarbyl, and silyl group;
$R^2$, $R^3$, $R^4$, $R^5$, and $R^6$ are independently selected from hydrogen, hydrocarbyl, alkoxy, silyl, amino, aryloxy, substituted hydrocarbyl, halogen, and phosphino;
optionally two adjacent R groups are joined to form a substituted or unsubstituted hydrocarbyl or heterocyclic ring, wherein the ring has 5, 6, 7, or 8 ring atoms and wherein substitutions on the ring can join to form additional rings;

J is

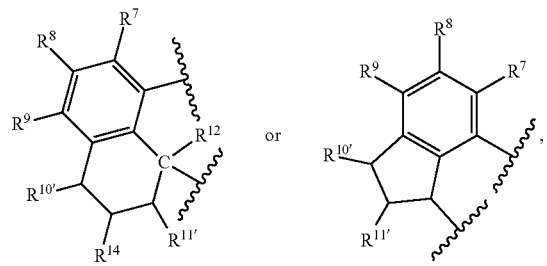

wherein $R^7$, $R^8$, $R^9$, $R^{10'}$, $R^{11'}$, and $R^{14}$ are independently hydrogen, hydrocarbyl, alkoxy, silyl, amino, aryloxy, substituted hydrocarbyl, halogen, or phosphino, and optionally any two R groups may be joined to form a substituted or unsubstituted hydrocarbyl or heterocyclic ring,
where the ring has 5, 6, 7, or 8 ring atoms, said ring is saturated or unsaturated, and wherein ⸯ indicates connection to the ligand;
said method comprising:
1) introducing an acid solution, a nitrite, and phosphorous oxoacid to a compound represented by Formula C or Formula K:

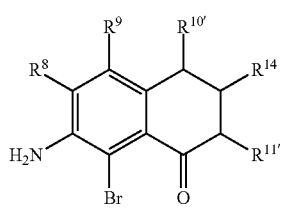

C

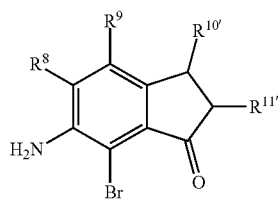

K wherein $R^8$, $R^9$, $R^{10'}$, $R^{11'}$, and $R^{14}$ are independently, as described above for J, and optionally any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated; and
2) obtaining a compound represented by Formula D or Formula L:

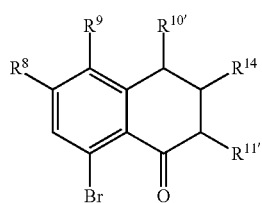

D

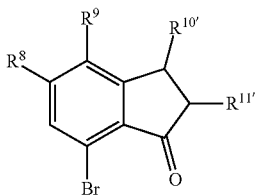

L wherein $R^8$, $R^9$, $R^{10'}$, $R^{11'}$, and $R^{14}$ are as described above for J, and optionally any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated;

3) introducing $TiCl_4$ and an aniline to the compound represented by Formula D or Formula L;
4) obtaining a compound represented by Formula E or Formula M:

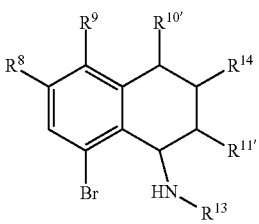

E

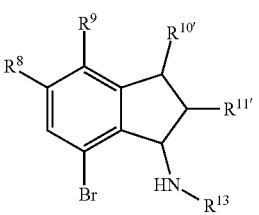

M wherein $R^{13}$ is as described for Formula (I), and $R^8$, $R^9$, $R^{10'}$, $R^{11'}$, and $R^{14}$ are independently as described above for J, and optionally any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated;

5) introducing lithiating agent and borolane to the compound represented by Formula E or Formula M; and
6) obtaining a compound represented by Formula F or Formula N:

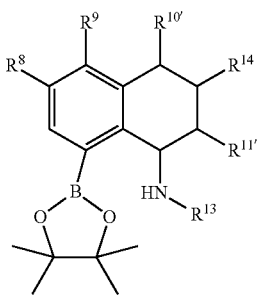

F

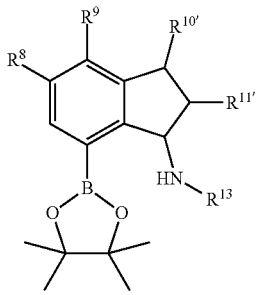

N wherein $R^{13}$ is selected from is as described above for Formula (I), and $R^8$, $R^9$, $R^{10'}$, and $R^{11'}$ are independently as described above for J, and optionally any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated;

7) introducing a base, a palladium agent, and the compound represented by Formula F or Formula N to a compound represented by Formula H:

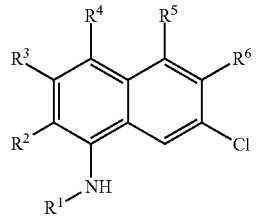

H wherein $R^1$ is as described above for Formula (I), and $R^2$, $R^3$, $R^4$, $R^5$, and $R^6$ are independently as described above for Formula (I), and optionally any two of $R^2$ & $R^3$, $R^3$ & $R^4$, and $R^5$ & $R^6$ are joined to form a substituted or unsubstituted hydrocarbyl or heterocyclic ring, wherein the ring has 5, 6, 7, or 8 ring atoms, and wherein the ring is saturated or unsaturated; and 8) obtaining the quinolinyldiamine.

2. The method of claim 1, wherein introducing in step 1) comprises:

mixing the acid solution with the compound represented by Formula C or Formula K to form a first mixture;

mixing the nitrite with the first mixture to form a second mixture; and mixing the phosphorous oxoacid with the second mixture to form a third mixture.

3. The method of claim 1, further comprising contacting the compound represented by Formula D or Formula L with an organic solvent.

4. The method of claim 3, wherein the organic solvent is an alcohol.

5. The method of claim 1, wherein the acid solution is a 2M to 6M solution of HCl.

6. The method of claim 1, wherein the nitrite is sodium nitrite, potassium nitrite, or mixtures thereof.

7. The method of claim 1, wherein the phosphorous oxoacid is hypophosphorous acid.

8. The method of claim 1, further comprising:
mixing the TiCl$_4$ with the aniline to form a fourth mixture;
heating the fourth mixture at a temperature of from about 30° C. to about 120° C.;
mixing the compound represented by Formula D or Formula L to form a fifth mixture;
heating the fifth mixture at a temperature of from about 30° C. to about 120° C.; and
obtaining a dried product from the fifth mixture.

9. The method of claim 8, further comprising introducing the dried product to a reducing agent and an acid.

10. The method of claim 9, wherein:
the reducing agent is selected from NaBH$_4$, NaBH$_3$CN, and LiAlH$_4$, and
the acid is acetic acid.

11. The method of claim 1, further comprising contacting the compound represented by Formula E or Formula M with an organic solvent.

12. The method of claim 11, wherein the organic solvent is an alcohol.

13. The method of claim 12, wherein introducing comprises:
mixing the lithiating agent and the compound represented by Formula E or Formula M to form a sixth mixture;
mixing the borolane with the sixth mixture to form a seventh mixture, and the sixth mixture is at a temperature of from about −100° C. to about 0° C.

14. The method of claim 1, wherein the borolane is 2-isopropoxy-4,4,5,5-tetramethyl-1,3,2-dioxaborolane.

15. The method of claim 1, further comprising contacting the compound represented by Formula F or Formula N with an organic solvent.

16. The method of claim 15, wherein the organic solvent is an alcohol.

17. The method of claim 1, wherein the base is cesium carbonate and the palladium agent is Pd(Ph$_3$)$_4$.

18. The method of claim 1, further comprising contacting the quinolinyldiamine with an organic solvent.

19. The method of claim 18, wherein the organic solvent is hexane.

20. The method of claim 1, further comprising:
introducing the quinolinyldiamine to a transition metal; and
obtaining a transition metal quinolinyldiamido complex.

21. The method of claim 20, wherein the metal quinolinyldiamido complex is:

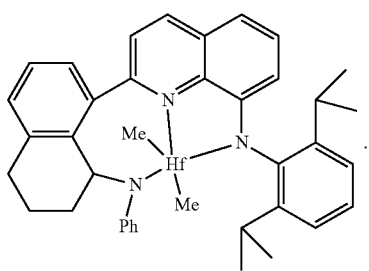

(2)

22. The method of claim 1, further comprising:
obtaining the compound represented by Formula C or Formula K by introducing a brominating agent to a compound represented by Formula B or Formula Q:

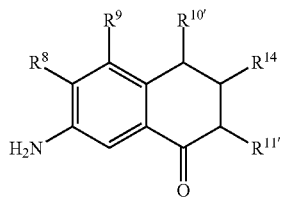

B

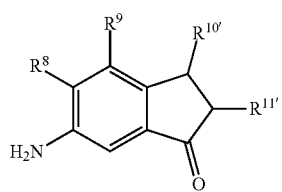

Q wherein $R^8$, $R^9$, $R^{10'}$, $R^{11'}$, and $R^{14}$ are independently hydrogen, hydrocarbyl, alkoxy, silyl, amino, aryloxy, substituted hydrocarbyl, halogen, or phosphino, or any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated.

23. The method of claim 22, wherein the brominating agent is N-bromosuccinimide.

24. The method of claim 1, further comprising:
obtaining the compound represented by Formula B or Formula Q by introducing a reducing agent to a compound represented by Formula A or Formula P:

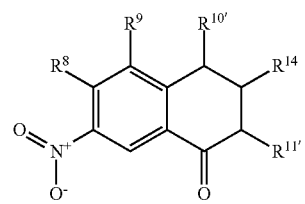

A

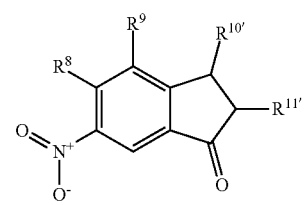

P wherein $R^8$, $R^9$, $R^{10'}$, $R^{11'}$, and $R^{14}$ are independently hydrogen, hydrocarbyl, alkoxy, silyl, amino, aryloxy, substituted hydrocarbyl, halogen, or phosphino, or any two of $R^8$ & $R^9$, $R^9$ & $R^{10'}$, $R^{10'}$ & $R^{14}$, and $R^{10'}$ & $R^{11'}$ are joined to form a substituted or unsubstituted hydrocarbyl or heterocyclic ring, wherein the ring has 5, 6, 7, or 8 ring atoms, and wherein the ring is saturated or unsaturated.

25. The method of claim 24, wherein the reducing agent is stannous chloride or stannous bromide.

26. The method of claim 24, further comprising contacting the compound represented by Formula B or Formula Q with an organic solvent.

27. The method of claim 26, wherein the organic solvent is an alcohol.

28. The method of claim 1, further comprising:
obtaining the compound represented by Formula A or Formula P by introducing a 3,4-dihydronaphtalene-1(2H)-one or a 2,3-dihydro-1H-inden-1-one to a nitrating agent and an acid.

29. The method of claim 28, wherein the nitrating agent is $KNO_3$ or $NaNO_3$ and the acid is sulfuric acid.

30. The method of claim 28, further comprising contacting the compound represented by Formula A or Formula P with an organic solvent.

31. The method of claim 30, wherein the organic solvent is an alcohol.

* * * * *